US012208260B2

(12) United States Patent
Sanghera et al.

(10) Patent No.: US 12,208,260 B2
(45) Date of Patent: Jan. 28, 2025

(54) IMPLANTABLE ELECTRICAL LEADS AND ELECTRODES

(71) Applicant: ATACOR MEDICAL, INC., San Clemente, CA (US)

(72) Inventors: Rick Sanghera, San Clemente, CA (US); Matthew Rollins, San Clemente, CA (US); John Beck, San Clemente, CA (US); William Born, San Clemente, CA (US); Shahn Sage, San Clemente, CA (US); Alan Marcovecchio, San Clemente, CA (US)

(73) Assignee: Kurin, Inc., San Diego, CA (US)

( * ) Notice: Subject to any disclaimer, the term of this patent is extended or adjusted under 35 U.S.C. 154(b) by 120 days.

(21) Appl. No.: 16/888,468

(22) Filed: May 29, 2020

(65) Prior Publication Data
US 2020/0398044 A1 Dec. 24, 2020

Related U.S. Application Data

(60) Provisional application No. 62/854,178, filed on May 29, 2019.

(51) Int. Cl.
A61N 1/05 (2006.01)
A61B 17/34 (2006.01)
(Continued)

(52) U.S. Cl.
CPC ........ A61N 1/0597 (2013.01); A61B 17/3468 (2013.01); A61N 1/05 (2013.01);
(Continued)

(58) Field of Classification Search
CPC .......... A61N 1/0597; A61N 1/05; A61N 1/37; A61N 1/362; A61N 1/3956; A61N 1/0587; A61B 17/3468; A61B 2017/00867
See application file for complete search history.

(56) References Cited

U.S. PATENT DOCUMENTS 2,003,007 A 5/1935 Morgan
3,416,534 A 12/1968 Quinn
(Continued)

FOREIGN PATENT DOCUMENTS

EP 0668087 8/1995
EP 1530983 A2 5/2005
(Continued)

OTHER PUBLICATIONS

Brown, Charles G., et al. 'Injuries Associated with Percutaneous Placement of Transthoracic Pacemakers.' Annals of Emergency Medicine 14.3 (1985): 223-28.
(Continued)

Primary Examiner — Brooke Labranche
(74) Attorney, Agent, or Firm — Pillsbury Winthrop Shaw Pittman LLP

(57) ABSTRACT

Systems, methods, and devices to facilitate insertion of certain leads with electrode(s) into patients are described. Leads can be implanted to work in conjunction with a cardiac pacemaker or cardiac defibrillator. A lead for cardiac therapy may be inserted into an intercostal space associated with the cardiac notch of a patient. Devices for delivery may include, for example, a delivery system coupled with an electrical lead and having a handle, a component advancer and insertion tips. The handle is configured to be actuated by an operator and the component advancer is configured to advance an electrical lead into the patient. The insertion tips can be configured to close around the electrical lead within the component advancer, to push through biological tissue, and to open to enable the lead to advance into the patient. The electrical lead can also be maintained in a particular orientation during the advancement into the patient.

6 Claims, 31 Drawing Sheets

(51) Int. Cl.
    *A61N 1/37*     (2006.01)
    *A61B 17/00*    (2006.01)

(52) U.S. Cl.
    CPC ...... *A61N 1/37* (2013.01); *A61B 2017/00367* (2013.01); *A61B 2017/00867* (2013.01)

(56) References Cited

U.S. PATENT DOCUMENTS

| | | |
|---|---|---|
| 3,485,247 A | 12/1969 | Ackerman |
| 4,030,509 A | 6/1977 | Heilman |
| 4,146,037 A | 3/1979 | Flynn |
| 4,270,549 A | 6/1981 | Heilman |
| 4,280,510 A | 7/1981 | ONeill |
| 4,291,707 A | 9/1981 | Heilman |
| 4,306,560 A | 12/1981 | Harris |
| 4,408,604 A | 10/1983 | Hirshorn |
| 4,437,475 A | 3/1984 | White |
| 4,502,492 A | 3/1985 | Bornzin |
| 4,512,351 A | 4/1985 | Pohndorf |
| 4,532,931 A | 8/1985 | Mills |
| 4,538,624 A | 9/1985 | Tarjan |
| 4,567,901 A | 2/1986 | Harris |
| 4,636,199 A | 1/1987 | Victor |
| 4,649,937 A | 3/1987 | DeHaan |
| 4,664,120 A | 5/1987 | Hess |
| 4,765,341 A | 8/1988 | Mower |
| 4,784,161 A | 11/1988 | Skalsky |
| 4,787,389 A | 11/1988 | Tarjan |
| 4,832,687 A | 5/1989 | Smith, III |
| 4,846,191 A | 7/1989 | Brockway |
| 4,865,037 A | 9/1989 | Chin |
| 4,967,746 A | 11/1990 | Vandegriff |
| 5,036,854 A | 8/1991 | Schollmeyer |
| 5,078,678 A | 1/1992 | Katims |
| 5,085,218 A | 2/1992 | Heil, Jr. |
| 5,125,904 A | 6/1992 | Lee |
| 5,129,394 A | 7/1992 | Mehra |
| 5,176,135 A | 1/1993 | Fain |
| 5,184,616 A | 2/1993 | Weiss |
| 5,203,348 A | 4/1993 | Dahl |
| 5,209,229 A | 5/1993 | Gilli |
| 5,224,475 A | 7/1993 | Berg |
| 5,231,996 A | 8/1993 | Bardy |
| 5,255,691 A | 10/1993 | Otten |
| 5,255,692 A | 10/1993 | Neubauer |
| 5,273,053 A | 12/1993 | Pohndorf |
| 5,300,106 A | 4/1994 | Dahl |
| 5,312,355 A | 5/1994 | Lee |
| 5,329,923 A * | 7/1994 | Lundquist ......... A61M 25/0147 607/122 |
| 5,336,252 A | 8/1994 | Cohen |
| 5,364,361 A | 11/1994 | Battenfield |
| 5,391,156 A | 2/1995 | Hildwein |
| 5,403,355 A | 4/1995 | Alt |
| 5,411,527 A | 5/1995 | Alt |
| 5,441,504 A | 8/1995 | Pohndorf |
| 5,456,699 A | 10/1995 | Armstrong |
| 5,476,493 A | 12/1995 | Muff |
| 5,509,924 A | 4/1996 | Paspa |
| 5,534,018 A | 7/1996 | Wahlstrand |
| 5,534,022 A | 7/1996 | Hoffmann |
| 5,545,205 A | 8/1996 | Schulte |
| 5,562,677 A | 10/1996 | Hildwein |
| 5,564,615 A | 10/1996 | Bishop |
| 5,571,215 A | 11/1996 | Sterman |
| 5,613,953 A | 3/1997 | Pohndorf |
| 5,626,587 A | 5/1997 | Bishop |
| 5,645,580 A | 7/1997 | Moaddeb |
| 5,662,662 A | 9/1997 | Bishop |
| 5,690,648 A | 11/1997 | Fogarty |
| 5,716,392 A | 2/1998 | Bourgeois |
| 5,728,151 A | 3/1998 | Garrison |
| 5,752,526 A | 5/1998 | Cosgrove |
| 5,752,970 A | 5/1998 | Yoon |
| 5,776,110 A | 7/1998 | Guy |
| 5,779,699 A | 7/1998 | Lipson |
| 5,814,076 A | 9/1998 | Brownlee |
| 5,823,946 A | 10/1998 | Chin |
| 5,830,214 A | 11/1998 | Flom |
| 5,871,532 A | 2/1999 | Schroeppel |
| 5,895,414 A | 4/1999 | Sanchez-Zambrano |
| 5,904,711 A | 5/1999 | Flom |
| 5,941,819 A | 8/1999 | Chin |
| 5,944,732 A | 8/1999 | Raulerson |
| 5,951,518 A | 9/1999 | Licata |
| 6,024,704 A | 2/2000 | Meador |
| 6,032,079 A | 2/2000 | KenKnight |
| 6,076,012 A | 6/2000 | Swanson |
| 6,099,547 A | 8/2000 | Gellman |
| 6,104,957 A | 8/2000 | Alo |
| 6,122,552 A | 9/2000 | Tockman |
| 6,134,478 A | 10/2000 | Spehr |
| 6,159,198 A | 12/2000 | Gardeski |
| 6,179,835 B1 | 1/2001 | Panescu |
| 6,183,485 B1 | 2/2001 | Thomason |
| 6,228,052 B1 | 5/2001 | Pohndorf |
| 6,251,418 B1 | 6/2001 | Ahern |
| 6,283,127 B1 | 9/2001 | Sterman |
| 6,324,414 B1 | 11/2001 | Gibbons |
| 6,415,187 B1 | 7/2002 | Kuzma |
| 6,445,954 B1 | 9/2002 | Olive |
| 6,478,028 B1 | 11/2002 | Paolitto |
| 6,497,651 B1 | 12/2002 | Kan |
| 6,544,247 B1 | 4/2003 | Gardeski |
| 6,575,919 B1 | 6/2003 | Reiley |
| 6,647,292 B1 | 11/2003 | Bardy |
| 6,650,945 B2 | 11/2003 | Helland |
| 6,651,672 B2 | 11/2003 | Roth |
| 6,706,052 B1 | 3/2004 | Chin |
| 6,718,203 B2 | 4/2004 | Weiner |
| 6,721,597 B1 | 4/2004 | Bardy |
| 6,730,083 B2 | 5/2004 | Freigang |
| 6,733,500 B2 | 5/2004 | Kelley |
| 6,749,574 B2 | 6/2004 | OKeefe |
| 6,770,070 B1 | 8/2004 | Balbierz |
| 6,772,014 B2 | 8/2004 | Coe |
| 6,836,687 B2 | 12/2004 | Kelley |
| 6,866,044 B2 | 3/2005 | Bardy |
| 6,868,291 B1 | 3/2005 | Bonner |
| 6,887,229 B1 | 5/2005 | Kurth |
| 6,889,093 B1 * | 5/2005 | Flammang ........... A61N 1/3918 607/122 |
| 6,890,295 B2 | 5/2005 | Michels |
| 6,918,908 B2 | 7/2005 | Bonner |
| 6,952,610 B2 | 10/2005 | Ostroff |
| 6,987,999 B1 | 1/2006 | Kroll |
| 6,999,819 B2 | 2/2006 | Swoyer |
| 7,033,326 B1 | 4/2006 | Pianca |
| 7,039,459 B2 | 5/2006 | Bardy |
| 7,039,465 B2 | 5/2006 | Bardy |
| 7,050,851 B2 | 5/2006 | Plombon |
| 7,065,410 B2 | 6/2006 | Bardy |
| 7,069,083 B2 | 6/2006 | Finch |
| 7,096,064 B2 | 8/2006 | Deno |
| 7,117,039 B2 | 10/2006 | Manning |
| 7,120,496 B2 | 10/2006 | Bardy |
| 7,146,212 B2 | 12/2006 | Bardy |
| 7,149,575 B2 | 12/2006 | Ostroff |
| 7,181,288 B1 | 2/2007 | Rezai |
| 7,184,830 B2 | 2/2007 | Echt |
| 7,191,015 B2 | 3/2007 | Lamson |
| 7,195,637 B2 | 3/2007 | Mika |
| 7,218,970 B2 | 5/2007 | Ley |
| 7,229,450 B1 | 6/2007 | Chitre |
| 7,239,925 B2 | 7/2007 | Bardy |
| 7,272,448 B1 | 9/2007 | Morgan |
| 7,288,096 B2 | 10/2007 | Chin |
| 7,316,667 B2 | 1/2008 | Lindstrom |
| 7,319,905 B1 | 1/2008 | Morgan |
| 7,322,960 B2 | 1/2008 | Yamamoto |
| 7,353,067 B1 | 4/2008 | Helland |
| 7,369,899 B2 | 5/2008 | Malinowski |
| 7,373,207 B2 | 5/2008 | Lattouf |
| 7,389,134 B1 | 6/2008 | Karicherla |

(56) References Cited

U.S. PATENT DOCUMENTS

| | | |
|---|---|---|
| 7,398,781 B1 | 7/2008 | Chin |
| 7,450,997 B1 | 11/2008 | Pianca |
| 7,496,408 B2 | 2/2009 | Ghanem |
| 7,499,758 B2 | 3/2009 | Cates |
| 7,503,920 B2 | 3/2009 | Siegal |
| 7,515,969 B2 | 4/2009 | Tockman |
| 7,539,542 B1 | 5/2009 | Malinowski |
| 7,546,165 B2 | 6/2009 | Zarembo |
| 7,627,375 B2 | 12/2009 | Bardy |
| 7,655,014 B2 | 2/2010 | Ko |
| 7,736,330 B2 | 6/2010 | Bardy |
| 7,751,885 B2 | 7/2010 | Bardy |
| 7,761,150 B2 | 7/2010 | Ghanem |
| 7,765,014 B2 | 7/2010 | Eversull |
| 7,794,407 B2 | 9/2010 | Rothenberg |
| 7,801,622 B2 | 9/2010 | Camps |
| 7,837,671 B2 | 11/2010 | Eversull |
| 7,846,088 B2 | 12/2010 | Ness |
| 7,850,610 B2 | 12/2010 | Ferek-Petric |
| 7,853,311 B1 | 12/2010 | Webb |
| 7,890,191 B2 | 2/2011 | Rutten |
| 7,908,015 B2 | 3/2011 | Lazeroms |
| 7,930,028 B2 | 4/2011 | Lang |
| 7,930,040 B1 | 4/2011 | Kelsch |
| 7,967,833 B2 | 6/2011 | Sterman |
| 7,983,765 B1 | 7/2011 | Doan |
| 8,060,207 B2 | 11/2011 | Wallace |
| 8,065,020 B2 | 11/2011 | Ley |
| 8,066,702 B2 | 11/2011 | Rittman, III |
| 8,090,451 B2 | 1/2012 | Tyson, Jr. |
| 8,155,755 B2 | 4/2012 | Flynn |
| 8,157,813 B2 | 4/2012 | Ko |
| 8,260,436 B2 | 9/2012 | Gerber |
| 8,280,527 B2 | 10/2012 | Eckerdal |
| 8,332,036 B2 | 12/2012 | Hastings |
| 8,340,779 B2 | 12/2012 | Harris |
| 8,355,786 B2 | 1/2013 | Malinowski |
| 8,386,052 B2 | 2/2013 | Harris |
| 8,394,079 B2 | 3/2013 | Drake |
| 8,435,208 B2 | 5/2013 | Bardy |
| 8,442,620 B2 | 5/2013 | Silipo |
| 8,452,421 B2 | 5/2013 | Thenuwara |
| 8,454,552 B2 | 6/2013 | Bardy |
| 8,457,742 B2 | 6/2013 | Jacobson |
| 8,478,424 B2 | 7/2013 | Tronnes |
| 8,478,426 B2 | 7/2013 | Barker |
| 8,478,431 B2 | 7/2013 | Griswold |
| 8,483,841 B2 | 7/2013 | Sanghera |
| 8,532,789 B2 | 9/2013 | Smits |
| 8,543,222 B1 | 9/2013 | Sochor |
| 8,594,809 B2 | 11/2013 | Yang |
| 8,626,287 B2 | 1/2014 | Hareland |
| 8,731,659 B2 | 5/2014 | Hansen |
| 8,886,311 B2 | 11/2014 | Anderson |
| 9,079,035 B2 | 7/2015 | Sanghera |
| 9,220,913 B2 | 12/2015 | Christie |
| 9,439,653 B2 | 9/2016 | Avneri |
| 9,468,754 B2 | 10/2016 | Martinez |
| 9,622,778 B2 | 4/2017 | Wengreen |
| 9,636,505 B2 | 5/2017 | Sanghera |
| 9,636,512 B2 | 5/2017 | Cinbis |
| 9,707,389 B2 | 7/2017 | McGeehan |
| 9,717,898 B2 | 8/2017 | Thompson-Nauman |
| 9,757,190 B2 | 9/2017 | Evans |
| 9,855,414 B2 | 1/2018 | Marshall |
| 10,022,539 B2 | 7/2018 | Sanghera |
| 10,080,905 B2 | 9/2018 | Anderson |
| 10,130,824 B2 | 11/2018 | Grinberg |
| 10,137,295 B2 | 11/2018 | Marshall |
| 10,471,267 B2 | 11/2019 | Thompson-Nauman |
| 10,532,203 B2 | 1/2020 | Thompson-Nauman |
| 10,556,117 B2 | 2/2020 | Thompson-Nauman |
| 10,661,073 B2 | 5/2020 | Marshall |
| 10,668,270 B2 | 6/2020 | Thompson-Nauman |
| 10,722,704 B2 | 7/2020 | Min |
| 10,758,228 B2 | 9/2020 | Zenz-Olson |
| 10,842,998 B2 | 11/2020 | Keefe |
| 10,881,850 B2 | 1/2021 | Baudino |
| 10,940,325 B2 | 3/2021 | Grinberg |
| 11,433,232 B2 | 9/2022 | Thompson-Nauman |
| 11,596,468 B2 | 3/2023 | Pellegrino |
| 11,666,771 B2 | 6/2023 | Sanghera |
| 2001/0001811 A1 | 5/2001 | Burney |
| 2002/0035381 A1 | 3/2002 | Bardy |
| 2002/0035388 A1 | 3/2002 | Lindemans |
| 2002/0042629 A1 | 4/2002 | Bardy |
| 2002/0042632 A1 | 4/2002 | Iaizzo |
| 2002/0072686 A1 | 6/2002 | Hoey |
| 2002/0072773 A1 | 6/2002 | Bardy |
| 2002/0120294 A1 | 8/2002 | Kroll |
| 2002/0133203 A1 | 9/2002 | Mouchawar |
| 2002/0143380 A1 | 10/2002 | Dahl |
| 2003/0045904 A1 | 3/2003 | Bardy |
| 2003/0074041 A1 | 4/2003 | Parry |
| 2003/0088278 A1 | 5/2003 | Bardy |
| 2003/0088301 A1 | 5/2003 | King |
| 2003/0097153 A1 | 5/2003 | Bardy |
| 2003/0114905 A1 | 6/2003 | Kuzma |
| 2003/0114906 A1 | 6/2003 | Booker |
| 2003/0114908 A1 | 6/2003 | Flach |
| 2003/0120264 A1 | 6/2003 | Lattouf |
| 2003/0130581 A1 | 7/2003 | Salo |
| 2003/0187458 A1 | 10/2003 | Carlson |
| 2003/0208153 A1 | 11/2003 | Stenzel |
| 2004/0059348 A1 | 3/2004 | Geske |
| 2004/0064176 A1 | 4/2004 | Min |
| 2004/0073261 A1 | 4/2004 | Kroll |
| 2004/0088035 A1 | 5/2004 | Guenst |
| 2004/0102829 A1 | 5/2004 | Bonner |
| 2004/0143254 A1 | 7/2004 | Vanney |
| 2004/0143284 A1 | 7/2004 | Chin |
| 2004/0158185 A1 | 8/2004 | Moran |
| 2004/0167416 A1 | 8/2004 | Lee |
| 2004/0210293 A1 | 10/2004 | Bardy |
| 2004/0215240 A1 | 10/2004 | Lovett |
| 2004/0230282 A1 | 11/2004 | Cates |
| 2004/0236396 A1 | 11/2004 | Coe |
| 2005/0027328 A1 | 2/2005 | Greenstein |
| 2005/0049663 A1 | 3/2005 | Harris |
| 2005/0075649 A1 | 4/2005 | Bova |
| 2005/0080470 A1 | 4/2005 | Westlund |
| 2005/0131505 A1 | 6/2005 | Yokoyama |
| 2005/0165324 A1 | 7/2005 | Receveur |
| 2005/0192639 A1 | 9/2005 | Bardy |
| 2005/0288731 A1 | 12/2005 | Shames |
| 2005/0288758 A1 | 12/2005 | Jones |
| 2006/0041295 A1 | 2/2006 | Osypka |
| 2006/0047333 A1 | 3/2006 | Tockman |
| 2006/0085039 A1 | 4/2006 | Hastings |
| 2006/0089699 A1 | 4/2006 | Imran |
| 2006/0116746 A1 | 6/2006 | Chin |
| 2006/0122676 A1 | 6/2006 | Ko |
| 2006/0129202 A1 | 6/2006 | Armstrong |
| 2006/0136004 A1 | 6/2006 | Cowan |
| 2006/0161205 A1 | 7/2006 | Mitrani |
| 2006/0224222 A1 | 10/2006 | Bradley |
| 2006/0241711 A1 | 10/2006 | Sathaye |
| 2006/0247672 A1 | 11/2006 | Vidlund |
| 2006/0247688 A1 | 11/2006 | Olson |
| 2006/0247753 A1 | 11/2006 | Wenger |
| 2006/0253181 A1 | 11/2006 | Schulman |
| 2006/0266368 A1 | 11/2006 | Heintz |
| 2007/0021736 A1 | 1/2007 | Johnson |
| 2007/0023947 A1 | 2/2007 | Ludwig |
| 2007/0043395 A1 | 2/2007 | Wei |
| 2007/0066998 A1 | 3/2007 | Hansen |
| 2007/0088394 A1 | 4/2007 | Jacobson |
| 2007/0088416 A1 | 4/2007 | Atalar |
| 2007/0100409 A1 | 5/2007 | Worley |
| 2007/0118034 A1 | 5/2007 | Mark |
| 2007/0150015 A1 | 6/2007 | Zhang |
| 2007/0150023 A1 | 6/2007 | Ignagni |
| 2007/0179388 A1 | 8/2007 | Larik |
| 2007/0197859 A1 | 8/2007 | Schaer |

(56) References Cited

U.S. PATENT DOCUMENTS

| | | |
|---|---|---|
| 2007/0208402 A1 | 9/2007 | Helland |
| 2007/0249992 A1 | 10/2007 | Bardy |
| 2008/0015590 A1 | 1/2008 | Sanders |
| 2008/0021505 A1 | 1/2008 | Hastings |
| 2008/0027488 A1 | 1/2008 | Coles |
| 2008/0039866 A1 | 2/2008 | Stetz |
| 2008/0046056 A1 | 2/2008 | OConnor |
| 2008/0103575 A1 | 5/2008 | Gerber |
| 2008/0146941 A1 | 6/2008 | Dala-Krishna |
| 2008/0183230 A1 | 7/2008 | Kemmetmueller |
| 2008/0183254 A1 | 7/2008 | Bly |
| 2008/0242976 A1 | 10/2008 | Robertson |
| 2008/0243196 A1 | 10/2008 | Libbus |
| 2008/0243219 A1 | 10/2008 | Malinowski |
| 2008/0269716 A1 | 10/2008 | Bonde |
| 2008/0294217 A1 | 11/2008 | Lian |
| 2008/0300644 A1 | 12/2008 | Sathaye |
| 2009/0000629 A1 | 1/2009 | Hornscheidt |
| 2009/0054947 A1 | 2/2009 | Bourn |
| 2009/0069803 A1 | 3/2009 | Starkebaum |
| 2009/0157091 A1 | 6/2009 | Buysman |
| 2009/0209854 A1 | 8/2009 | Parihar |
| 2009/0209970 A1 | 8/2009 | Tanaka |
| 2009/0222021 A1 | 9/2009 | Chang |
| 2009/0259283 A1 | 10/2009 | Brandt |
| 2009/0264780 A1 | 10/2009 | Schilling |
| 2009/0270962 A1 | 10/2009 | Yang |
| 2009/0326346 A1 | 12/2009 | Kracker |
| 2010/0016935 A1 | 1/2010 | Strandberg |
| 2010/0030227 A1 | 2/2010 | Kast |
| 2010/0030228 A1 | 2/2010 | Havel |
| 2010/0042110 A1 | 2/2010 | Kelley |
| 2010/0056858 A1 | 3/2010 | Mokelke |
| 2010/0082087 A1 | 4/2010 | Silipo |
| 2010/0094252 A1 | 4/2010 | Wengreen |
| 2010/0113963 A1 | 5/2010 | Smits |
| 2010/0125194 A1 | 5/2010 | Bonner |
| 2010/0137879 A1 | 6/2010 | Ko |
| 2010/0137949 A1 | 6/2010 | Mazgalev |
| 2010/0152747 A1 | 6/2010 | Padiy |
| 2010/0152798 A1 | 6/2010 | Sanghera |
| 2010/0152799 A1 | 6/2010 | Sanghera |
| 2010/0185268 A1 | 7/2010 | Fowler |
| 2010/0198041 A1 | 8/2010 | Christian |
| 2010/0211064 A1 | 8/2010 | Mahapatra |
| 2010/0217298 A1 | 8/2010 | Bardy |
| 2010/0217301 A1 | 8/2010 | Bardy |
| 2010/0241189 A1 | 9/2010 | Dobak |
| 2010/0305428 A1 | 12/2010 | Bonner |
| 2010/0318098 A1 | 12/2010 | Lund |
| 2010/0324579 A1 | 12/2010 | Bardy |
| 2010/0331868 A1 | 12/2010 | Bardy |
| 2010/0331938 A1 | 12/2010 | Sommer |
| 2011/0009933 A1 | 1/2011 | Barker |
| 2011/0024491 A1 | 2/2011 | Jamali |
| 2011/0066185 A1 | 3/2011 | Wotton, III |
| 2011/0071540 A1 | 3/2011 | Kast |
| 2011/0077708 A1 | 3/2011 | Ostroff |
| 2011/0093034 A1 | 4/2011 | Kast |
| 2011/0125163 A1 | 5/2011 | Rutten |
| 2011/0152706 A1 | 6/2011 | Christopherson |
| 2011/0155780 A1 | 6/2011 | Boudreaux |
| 2011/0178566 A1 | 7/2011 | Stahmann |
| 2011/0208261 A1 | 8/2011 | Levine |
| 2011/0210156 A1 | 9/2011 | Smith |
| 2011/0224680 A1 | 9/2011 | Barker |
| 2011/0224681 A1 | 9/2011 | McDonald |
| 2011/0230906 A1 | 9/2011 | Modesitt |
| 2011/0257660 A1 | 10/2011 | Jones |
| 2011/0257717 A1 | 10/2011 | Zimmerman |
| 2011/0319782 A1 | 12/2011 | Sweeney |
| 2012/0016377 A1 | 1/2012 | Geroy |
| 2012/0029335 A1 | 2/2012 | Sudam |
| 2012/0029342 A1 | 2/2012 | Kondabatni |
| 2012/0035697 A1* | 2/2012 | Stone ............ A61N 1/08 607/116 |
| 2012/0037291 A1 | 2/2012 | Goolishian |
| 2012/0078266 A1 | 3/2012 | Tyson |
| 2012/0089153 A1 | 4/2012 | Christopherson |
| 2012/0097174 A1 | 4/2012 | Spotnitz |
| 2012/0109250 A1 | 5/2012 | Cates |
| 2012/0123496 A1 | 5/2012 | Schotzko |
| 2012/0130465 A1 | 5/2012 | Risi |
| 2012/0191106 A1 | 7/2012 | Ko |
| 2012/0209283 A1 | 8/2012 | Zhu |
| 2012/0209298 A1 | 8/2012 | McClurg |
| 2012/0245433 A1 | 9/2012 | Ahern |
| 2012/0290053 A1 | 11/2012 | Zhang |
| 2012/0302863 A1 | 11/2012 | O'Neill |
| 2012/0323513 A1 | 12/2012 | Garai |
| 2013/0006326 A1 | 1/2013 | Ackermann |
| 2013/0041345 A1 | 2/2013 | Kilcoin |
| 2013/0060149 A1 | 3/2013 | Song |
| 2013/0090676 A1 | 4/2013 | Journey |
| 2013/0103049 A1 | 4/2013 | Bonde |
| 2013/0116529 A1 | 5/2013 | Xiaoyi |
| 2013/0158564 A1 | 6/2013 | Harris |
| 2013/0158621 A1 | 6/2013 | Ding |
| 2013/0178711 A1 | 7/2013 | Avneri |
| 2013/0178871 A1 | 7/2013 | Koogle, Jr. |
| 2013/0226266 A1 | 8/2013 | Murtonen |
| 2013/0237781 A1 | 9/2013 | Gyrn |
| 2013/0238067 A1 | 9/2013 | Baudino |
| 2013/0253531 A1 | 9/2013 | Kawaura |
| 2013/0261597 A1 | 10/2013 | Spedden |
| 2013/0261687 A1 | 10/2013 | Xi |
| 2013/0296880 A1 | 11/2013 | Kelley |
| 2013/0327342 A1 | 12/2013 | Watschke |
| 2013/0338707 A1 | 12/2013 | Killion |
| 2014/0005755 A1 | 1/2014 | Wolf, II |
| 2014/0018872 A1 | 1/2014 | Siejko |
| 2014/0039312 A1 | 2/2014 | Rockweiller |
| 2014/0121716 A1 | 5/2014 | Casavant |
| 2014/0180273 A1 | 6/2014 | Nair |
| 2014/0200602 A1 | 7/2014 | Saad |
| 2014/0243844 A1 | 8/2014 | Clancy |
| 2014/0257421 A1 | 9/2014 | Sanghera |
| 2014/0277311 A1 | 9/2014 | Victorine |
| 2014/0330208 A1 | 11/2014 | Christie |
| 2014/0330248 A1 | 11/2014 | Thompson-Nauman |
| 2014/0330287 A1 | 11/2014 | Thompson-Nauman |
| 2014/0330325 A1 | 11/2014 | Thompson-Nauman |
| 2014/0330326 A1 | 11/2014 | Thompson-Nauman |
| 2014/0330327 A1 | 11/2014 | Thompson-Nauman |
| 2014/0330328 A1 | 11/2014 | Christie |
| 2014/0330329 A1 | 11/2014 | Thompson-Nauman |
| 2014/0330331 A1 | 11/2014 | Thompson-Nauman |
| 2015/0013689 A1 | 1/2015 | Shackelford |
| 2015/0018634 A1 | 1/2015 | Zhu |
| 2015/0051612 A1 | 2/2015 | Schmidt |
| 2015/0051615 A1 | 2/2015 | Schmidt |
| 2015/0080995 A1 | 3/2015 | Seeley |
| 2015/0088155 A1 | 3/2015 | Stahmann |
| 2015/0133954 A1 | 5/2015 | Seifert |
| 2015/0142069 A1 | 5/2015 | Sambelashvili |
| 2015/0151114 A1 | 6/2015 | Black |
| 2015/0157497 A1 | 6/2015 | Hufford |
| 2015/0223906 A1 | 8/2015 | O'Neill |
| 2015/0290454 A1 | 10/2015 | Tyler |
| 2015/0313633 A1 | 11/2015 | Gross |
| 2015/0328473 A1 | 11/2015 | Bodner |
| 2016/0051159 A1 | 2/2016 | Mazaeva |
| 2016/0067478 A1 | 3/2016 | McGeehan |
| 2016/0067479 A1 | 3/2016 | Marcovecchio |
| 2016/0067480 A1 | 3/2016 | Sanghera |
| 2016/0067488 A1 | 3/2016 | Sanghera |
| 2016/0144192 A1 | 5/2016 | Sanghera |
| 2016/0174860 A1 | 6/2016 | Lotfi |
| 2016/0175007 A1 | 6/2016 | Valbuena |
| 2016/0175580 A1 | 6/2016 | Marshall |
| 2016/0175581 A1 | 6/2016 | Gordon |
| 2016/0184047 A1 | 6/2016 | Weir |
| 2016/0339239 A1 | 11/2016 | Yoo |

(56) References Cited

U.S. PATENT DOCUMENTS

| | | |
|---|---|---|
| 2016/0346059 A1 | 12/2016 | McNeely |
| 2017/0165470 A1 | 6/2017 | Jeffery |
| 2017/0224995 A1 | 8/2017 | Sanghera |
| 2017/0259078 A1 | 9/2017 | Howard |
| 2017/0304019 A1 | 10/2017 | Sanghera |
| 2017/0304634 A1 | 10/2017 | Sanghera |
| 2018/0021572 A1 | 1/2018 | McGeehan |
| 2018/0028804 A1* | 2/2018 | Pianca ............... A61B 17/3468 |
| 2018/0050199 A1 | 2/2018 | Sanghera |
| 2018/0117308 A1 | 5/2018 | Remmert |
| 2018/0193060 A1* | 7/2018 | Reddy ................ A61N 1/3621 |
| 2019/0105489 A1 | 4/2019 | Thompson-Nauman |
| 2019/0351221 A1 | 11/2019 | Ganty |
| 2020/0376265 A1 | 12/2020 | Sanghera |
| 2021/0113295 A1 | 4/2021 | Sanghera |
| 2021/0187313 A1 | 6/2021 | Grinberg |
| 2021/0370053 A1 | 12/2021 | Jin |
| 2021/0370080 A1 | 12/2021 | Sanghera |
| 2021/0370081 A1 | 12/2021 | Sanghera |
| 2022/0095980 A1 | 3/2022 | Scharf |

FOREIGN PATENT DOCUMENTS

| | | |
|---|---|---|
| EP | 2346419 | 7/2011 |
| EP | 2464418 | 6/2012 |
| EP | 2967644 | 1/2016 |
| EP | 2994193 | 3/2016 |
| EP | 2994194 | 3/2016 |
| EP | 3173043 | 5/2017 |
| EP | 3429686 | 1/2019 |
| WO | 2002026315 A1 | 4/2002 |
| WO | 2006115772 A2 | 11/2006 |
| WO | 2009134960 | 11/2009 |
| WO | 2009148941 | 12/2009 |
| WO | 2013163267 A1 | 10/2013 |
| WO | 2015143327 | 9/2015 |
| WO | 2017198472 | 11/2017 |
| WO | 2018009913 | 1/2018 |

OTHER PUBLICATIONS

Brown, Charles G., et al. 'Placement Accuracy of Percutaneous Transthoracic Pacemakers.' The American Journal of Emergency Medicine 3.3 (1985): 193-98.

Nagdev, Arun, and Daniel Mantuani. 'A Novel In-plane Technique for Ultrasound-guided Pericardiocentesis.' Tlie American Journal of Emergency Medicine 31.9 (2013): 1424.e5-1424.e9.

Pai, N. V., et al. 'Relation of Internal Thoracic Artery to Lateral Sternal Border and Its Significance in Clinical Procedures.' International Journal of Biological & Medical Research 4.4 (2013): 3633-636.

PCT/US2017/041265; International Search Report and Written Opinion mailed Sep. 25, 2017; 11 pages.

Office Action dated Feb. 28, 2020 for U.S. Appl. No. 14/846,578 (pp. 1-8).

Notice of Allowance dated Apr. 13, 2020 for U.S. Appl. No. 15/644,714 (pp. 1-9).

Office Action dated May 14, 2020 for U.S. Appl. No. 16/267,255 (pp. 1-8).

International Search Report and Written Opinion mailed Sep. 21, 2020, International Application No. PCT/US2020/035268.

International Search Report and Written Opinion mailed Jan. 24, 2022, International application No. PCT/IB2021/056065.

International Preliminary Report on Patentability mailed Jan. 19, 2023, International application No. PCT/IB2021/056065.

European Search Report dated Jul. 14, 2023, for EP Patent Application No. 23158313.9. 167 pages.

* cited by examiner

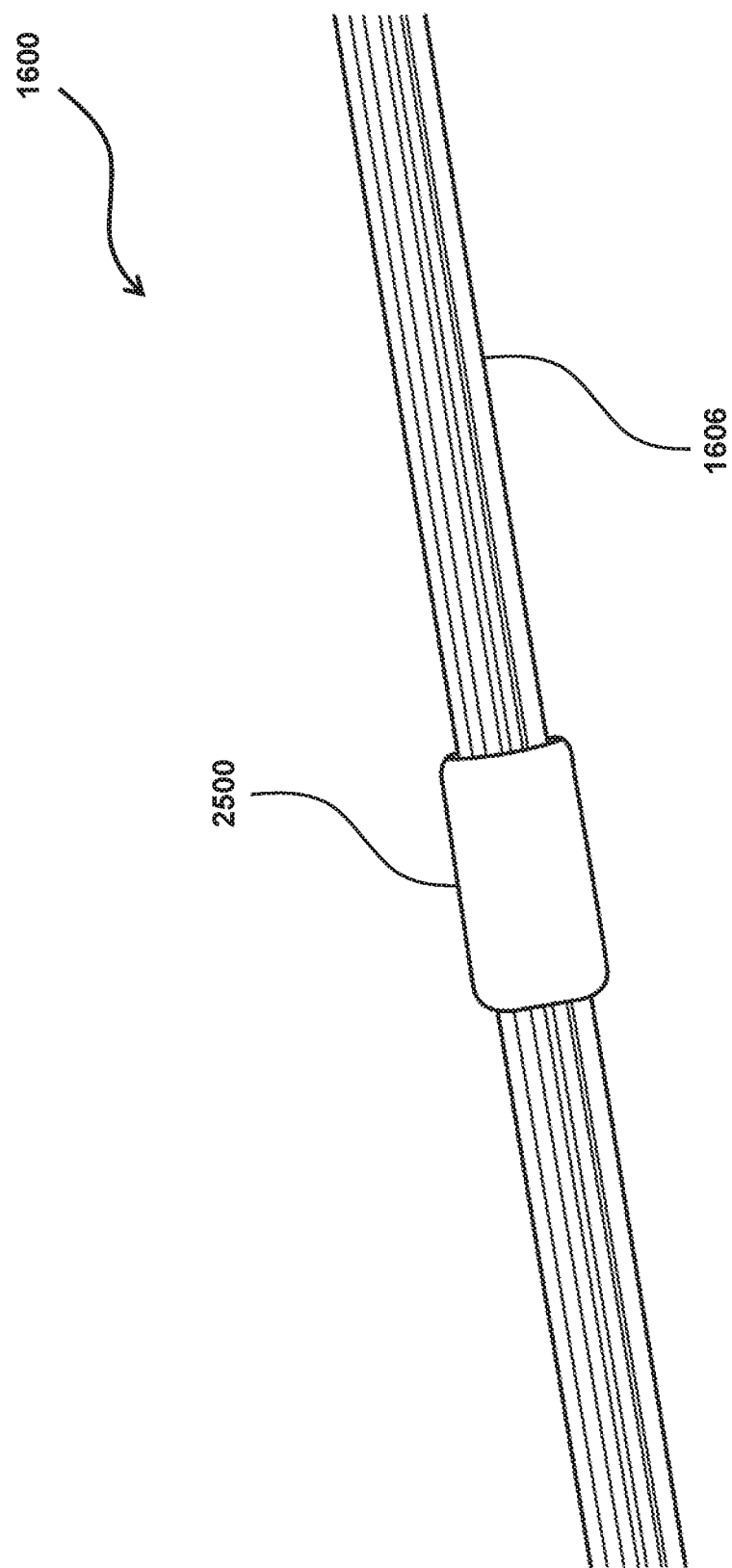

IMPLANTABLE ELECTRICAL LEADS AND ELECTRODES

CROSS-REFERENCE TO RELATED APPLICATIONS

This application claims the benefit of U.S. Provisional Patent Application No. 62/854,178, filed May 29, 2019, the disclosure of which is incorporated herein by reference in its entirety.

DESCRIPTION OF THE RELATED ART

Electrical leads can be implanted in patients for a variety of medical purposes. In one particular application, leads can be implanted to work in conjunction with a cardiac pacemaker or cardiac defibrillator. Pacemakers and cardiac defibrillators are medical devices that help control abnormal heart rhythms. A pacemaker uses electrical pulses to prompt the heart to beat at a normal rate. The pacemaker may speed up a slow heart rhythm, control a fast heart rhythm, and/or coordinate the chambers of the heart. The portions of a pacemaker system generally comprise three main components: a pulse generator, one or more wires called leads, and electrode(s) found on each lead.

The pulse generator produces the electrical signals that help regulate the heartbeat. Most pulse generators also have the capability to receive and respond to signals that come from the heart. Leads are generally flexible wires that conduct electrical signals from the pulse generator toward the heart. One end of the lead is attached to the pulse generator and the other end of the lead, containing the electrode(s) is positioned on, in or near the heart.

While the present disclosure refers to cardiac pacing, it is contemplated that the lead and delivery system technologies described herein can be used in other applications such as cardiac defibrillation as well.

SUMMARY

Systems, methods, and devices to facilitate insertion of certain leads with electrode(s) into patients for a variety of medical purposes are described. In some implementations, leads can be implanted to work in conjunction with a cardiac pacemaker or cardiac defibrillator. In such implementations, a lead for cardiac therapy may be inserted into an intercostal space associated with the cardiac notch of a patient.

For example, the described systems, methods, and devices may include a delivery system. In some implementations, the delivery system may include a handle, a component advancer, first and second insertion tips, and/or other components. The handle may be configured to be actuated by an operator. The component advancer may be configured to advance a component into a patient. The component advancer may be configured to removably engage a portion of the component. The component advancer may be coupled to the handle and configured to advance the component into the patient by applying a force to the portion of the component in response to actuation of the handle by the operator. The first insertion tip and the second insertion tip may be configured to close around a distal tip of the component when the component is placed within the component advancer. The first insertion tip and the second insertion tip may be further configured to push through biological tissue when in a closed position and to open to enable the component to exit from the component advancer into the patient.

In some implementations, the component may be an electrical lead for cardiac therapy.

In some implementations, the component advancer may include a pusher tube coupled with the handle such that actuation of the handle by the operator causes movement of the pusher tube to push on the portion of the component to advance the component into the patient.

In some implementations, the pusher tube may include a notch having a shape complementary to the portion of the component and configured to maintain the component in a particular orientation so as to avoid rotation of the component within the device.

In some implementations, the first and second insertion tips may each include a channel at least partially complimentary to a shape of the component and configured to guide the component into the patient.

In some implementations, an insertion tip may include a ramped portion configured to facilitate advancement of the component into the patient in a particular direction.

In some implementations, the delivery system may include the handle, the component advancer, a (unitary) insertion tip, and/or other components. The insertion tip may be configured to hold the distal tip of the component when the component is placed within the component advancer. The insertion tip may be configured to push through the biological tissue. The insertion tip may include a distal orifice configured to enable the component to exit from the component advancer into the patient.

In some implementations, the delivery system may include the electrical lead, the handle, the component advancer, the first and second insertion tips, and/or other components. The electrical lead may include one or more electrodes configured to generate therapeutic energy for biological tissue of the patient. The handle may be configured to be actuated by the operator. The component advancer may be configured to advance the electrical lead into the patient. The component advancer may be configured to removably engage a portion of the electrical lead. The component advancer may be coupled to the handle and configured to advance the electrical lead into the patient by applying a force to the portion of the electrical lead in response to actuation of the handle by the operator. The first insertion tip and the second insertion tip may be configured to close around a distal tip of the electrical lead when the electrical lead is placed within the component advancer. The first insertion tip and the second insertion tip may be further configured to push through the biological tissue when in a closed position and to open to enable the electrical lead to exit from the component advancer into the patient. The component advancer, the first insertion tip, and the second insertion tip may be configured to maintain the electrical lead in a particular orientation during the exit of the component from the component advancer into the patient.

As another example, the described systems, methods, and devices may include the electrical lead, for implantation in a patient. The lead may include a distal portion, one or more electrodes, a proximal portion, and/or other components. The distal portion may be configured to engage the component advancer of the delivery system. The component advancer may be configured to advance the lead into the patient. The one or more electrodes may be coupled to the distal portion. The one or more electrodes may be configured to generate therapeutic energy for the biological tissue of the patient. The proximal portion may be coupled to the distal portion. The proximal portion may be configured to engage a controller when the lead is implanted in the patient. The controller may be configured to cause the electrode to generate the therapeutic energy. The distal portion may comprise a proximal shoulder. The proximal shoulder may be configured to engage the component advancer such that the lead is maintained in a particular orientation when the lead is advanced into the patient.

In some implementations, the electrical lead may comprise the distal portion, the proximal portion, and/or other components. The distal portion may comprise the one or more electrodes. The one or more electrodes may be configured to generate the therapeutic energy for the biological tissue of the patient. The proximal portion may be coupled to the distal portion and configured to engage the controller when the lead is implanted in the patient. The controller may be configured to cause the electrode to generate the therapeutic energy. At least a portion of the distal portion of the lead may comprise two parallel planar surfaces. The one or more electrodes may be located on one of the parallel planar surfaces.

In some implementations, the electrical lead may comprise the distal portion, the proximal portion, and/or other components. The distal portion may comprise the one or more electrodes. The one or more electrodes may be configured to generate the therapeutic energy for the biological tissue of the patient. The proximal portion may be coupled to the distal portion and configured to engage the controller when the lead is implanted in the patient. The controller may be configured to cause the electrode to generate the therapeutic energy. The distal portion may include a distal end. The distal end may include a flexible portion so as to allow the distal end to change course when encountering sufficient resistance traveling through the biological tissue of the patient.

In some implementations, the electrical lead may comprise the distal portion, the proximal portion, and/or other components. The distal portion may comprise the one or more electrodes. The one or more electrodes may be configured to generate the therapeutic energy for the biological tissue of the patient. The proximal portion may be coupled to the distal portion and configured to engage the controller when the lead is implanted in the patient. The controller may be configured to cause the electrode to generate the therapeutic energy. The distal portion may comprise a shape memory material configured to bend in a predetermined direction when the lead exits a delivery system. The distal portion may be configured to move in an opposite direction, from a first position to a second position in the patient.

In some implementations, the distal portion may be configured to move from the first position to the second position responsive to the shape memory material being heated to body temperature.

In some implementations, the electrical lead includes the distal portion, the proximal portion, and/or other components. The distal portion may include the one or more electrodes coupled to the distal portion. The one or more electrodes may be configured to generate the therapeutic energy for the biological tissue of the patient. The one or more electrodes may include one or both of corners and edges configured to enhance a current density in the one or more electrodes. The proximal portion may be coupled to the distal portion. The proximal portion may be configured to engage a controller when the lead is implanted in the patient. The controller may be configured to cause the one or more electrodes to generate the therapeutic energy.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 25 illustrates an example of an alignment block coupled to a proximal portion of an electrical lead, in accordance with certain aspects of the disclosure.

DETAILED DESCRIPTION

Implantable medical devices such as cardiac pacemakers or implantable cardioverter defibrillators (ICDs) may provide therapeutic electrical stimulation to the heart of a patient. The electrical stimulation may be delivered in the form of electrical pulses or shocks for pacing, cardioversion or defibrillation. This electrical stimulation is typically delivered via electrodes on one or more implantable leads that are positioned in, on or near the heart.

In one particular implementation discussed herein, a lead may be inserted in the region of the cardiac notch of a patient so that the distal end of the lead is positioned within the mediastinum, adjacent to the heart. For example, the distal end of the lead may be positioned in the anterior mediastinum, beneath the patient's sternum. The distal end of the lead can also be positioned so to be aligned with an intercostal space in the region of the cardiac notch. Other similar placements in the region of the cardiac notch, adjacent the heart, are also contemplated for this particular application of cardiac pacing.

Figure 1:
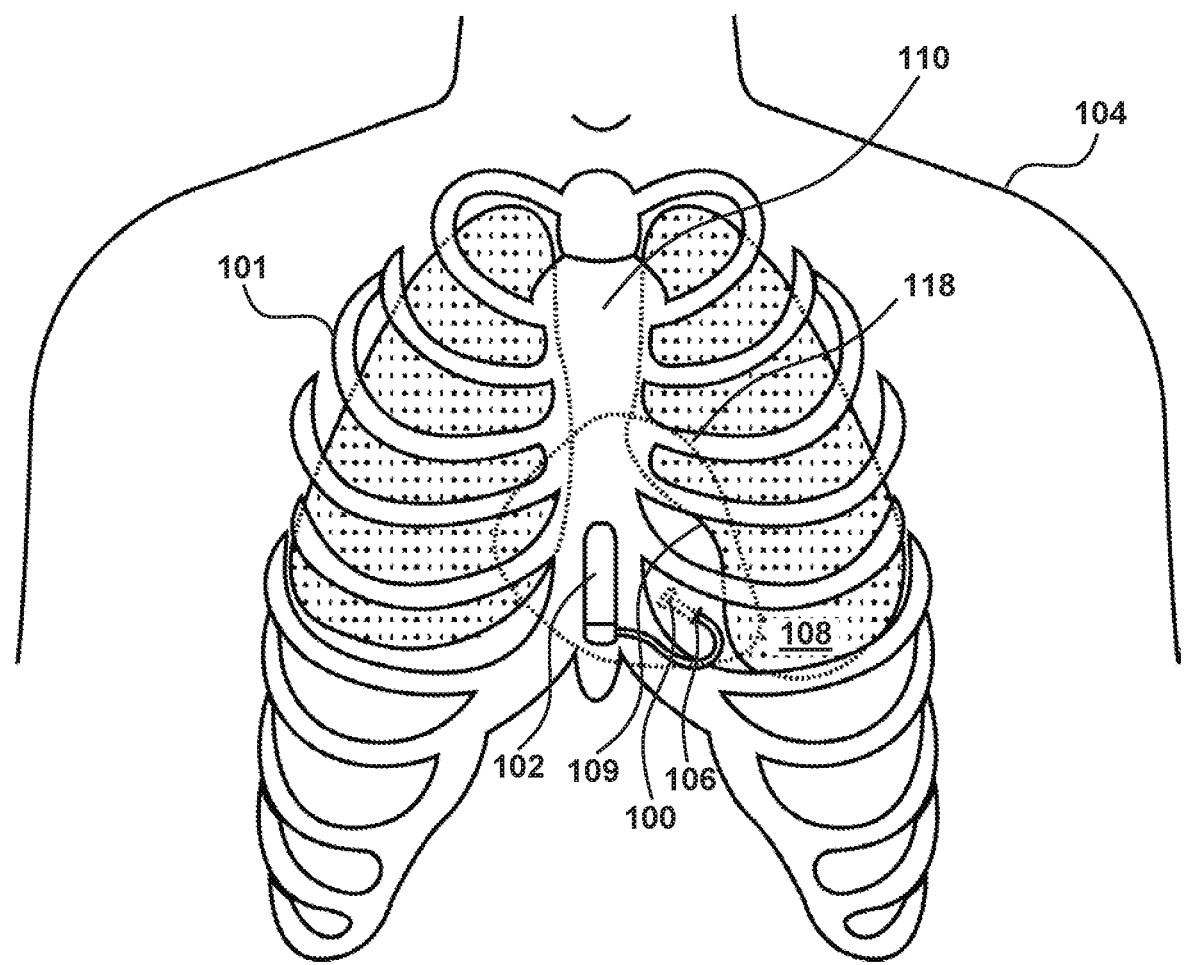
FIG. 1 is a diagram illustrating exemplary placements of elements of a cardiac pacing system, in accordance with certain aspects of the present disclosure.

In one exemplary procedure, as shown in FIG. 1, a cardiac pacing lead 100 may be inserted within the ribcage 101 of a patient 104 through an intercostal space 108 in the region of the cardiac notch. Lead 100 may be inserted through an incision 106, for example. The incision 106 may be made in proximity to the sternal margin to increase the effectiveness in finding the appropriate intercostal space 108 and avoiding certain anatomical features, for example the lung 109. The incision may be made lateral to the sternal margin, adjacent the sternal margin or any other direction that facilitates access to an appropriate intercostal space 108. A distal end of lead 100 can be positioned to terminate within the mediastinum of the thoracic cavity of the patient, proximate the heart 118. Lead 100 may then be connected to a pulse generator or controller 102, which may be placed above the patient's sternum 110. In alternative procedures, for temporary pacing, a separate controller may be used that is not implanted in the patient.

In some implementations, the pericardium is not invaded by the lead during or after implantation. In other implementations, incidental contact with the pericardium may occur, but heart 118 (contained within the pericardium) may remain untouched. In still further procedures, epicardial leads, or leads that reside within the pericardium, which do invade the pericardium, may be inserted.

Figure 2A:
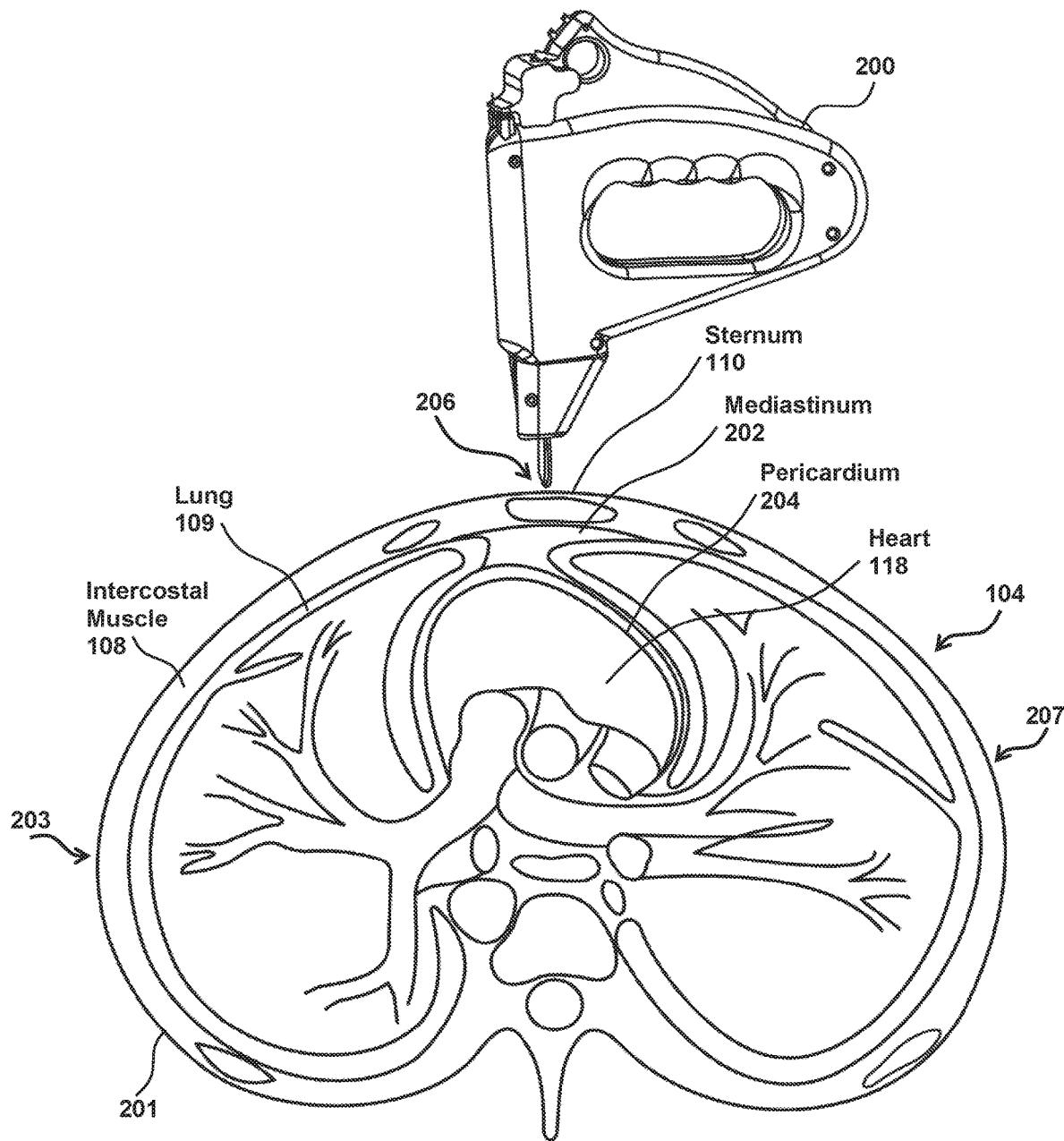
FIG. 2A is an illustration of an exemplary lead delivery system facilitating delivery of a cardiac pacing lead in the region of a cardiac notch, in accordance with certain aspects of the present disclosure.

FIG. 2A is an illustration of an exemplary lead delivery system 200 facilitating delivery of a lead in the region of a cardiac notch. FIG. 2A illustrates delivery system 200 and a cross section 201 (including left chest 203 and right chest 207) of a patient 104. FIG. 2A illustrates sternum 110, lung 109, intercostal muscle 108, heart 118, mediastinum 202, pericardium 204, and other anatomical features. As shown in FIG. 2A, lead delivery system 200 may be configured to allow for a distal end 206 of delivery system 200 to be pressed against the sternum 110 of patient 104.

Figure 2B:
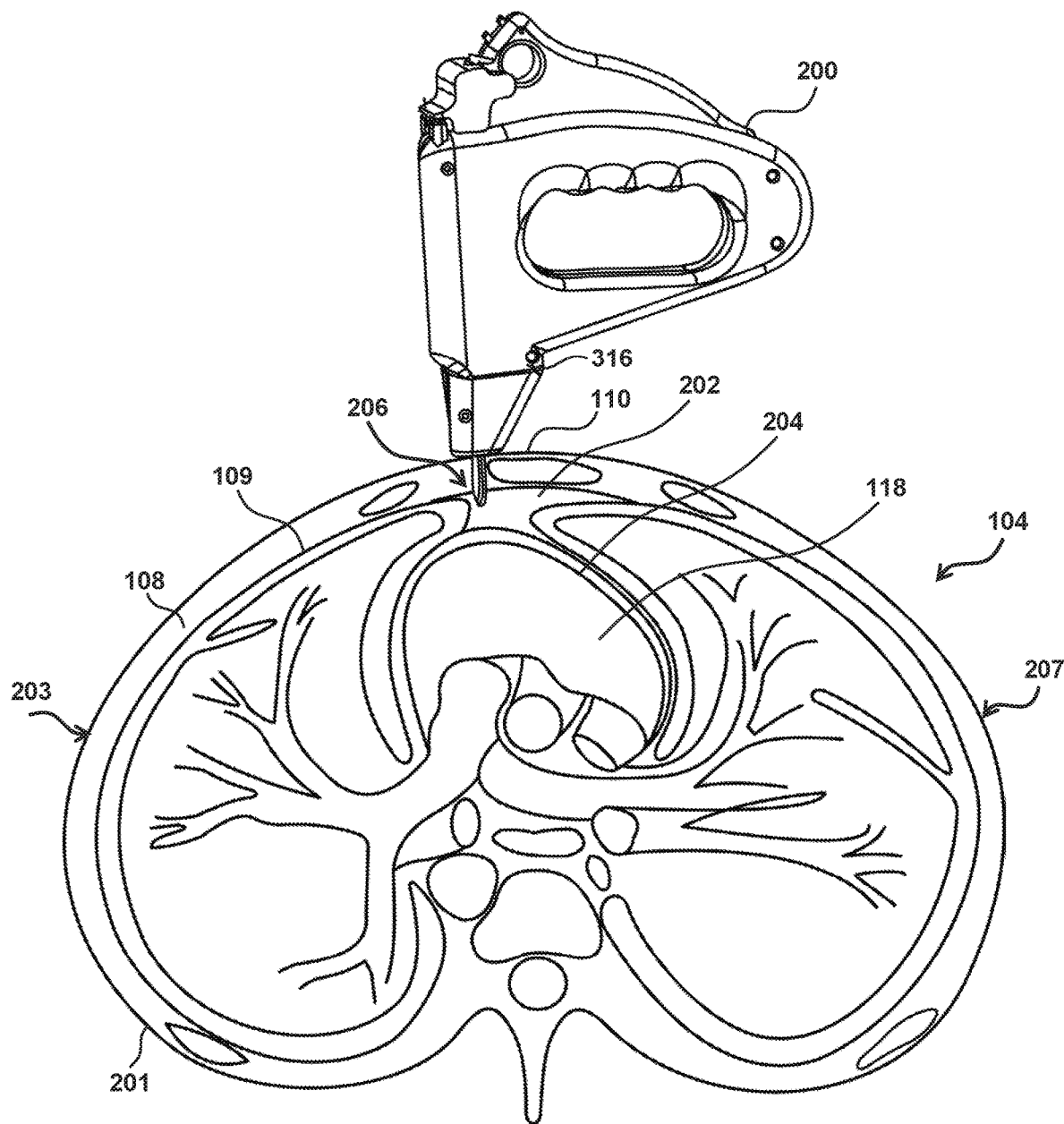
FIG. 2B illustrates a distal end of an exemplary lead delivery system having dropped into an intercostal space in the region of the cardiac notch, in accordance with certain aspects of the present disclosure.

In one implementation, a physician identifies an insertion point above or adjacent to a patient's sternum 110 and makes an incision. The distal end 206 of delivery system 200 can then be inserted through the incision, until making contact with sternum 110. The physician can then slide distal end 206 of delivery system 200 across sternum 110 toward the sternal margin until it drops through the intercostal muscle 108 in the region of the cardiac notch under pressure applied to the delivery system 200 by the physician. FIG. 2B illustrates the distal end 206 having dropped through the intercostal muscle in the region of the cardiac notch toward the pericardium.

In certain implementations, delivery system 200 may include an orientation or level guide 316 to aid the physician with obtaining the proper orientation and/or angle of delivery system 200 to the patient. Tilting delivery system 200 to the improper angle may negatively affect the deployment angle of lead 100 into the patient. For example, a horizontal level guide 316 on delivery system 200 helps to ensure that the physician keeps delivery system 200 level with the patient's sternum thereby ensuring lead 100 is delivered at the desired angle.

Figure 2C:
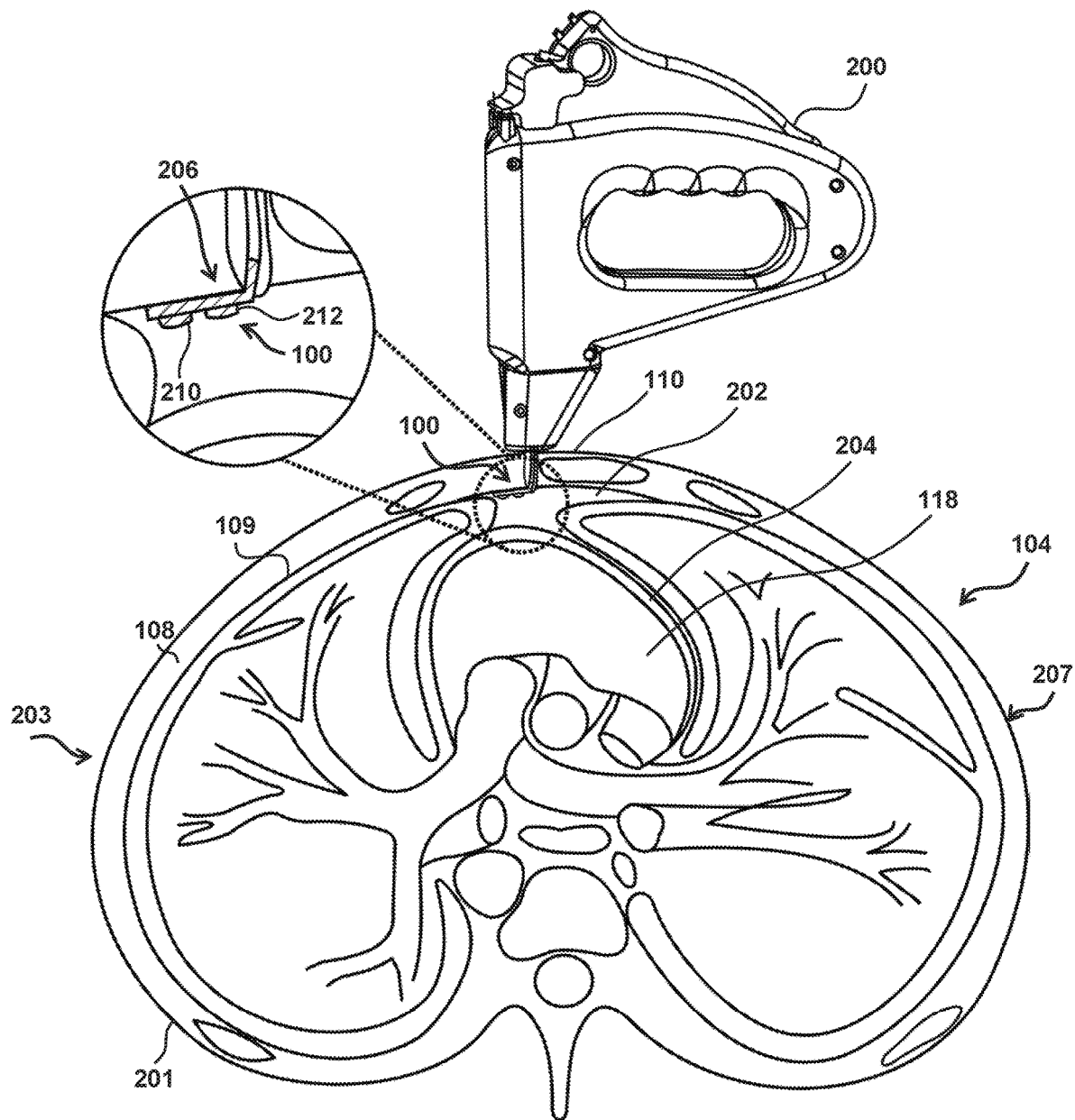
FIG. 2C illustrates an electrical lead exiting the exemplary delivery system with two electrodes positioned on a side of the lead facing the heart, in accordance with certain aspects of the present disclosure.

Following this placement of delivery system 200, the system may be actuated to insert an electrical lead 100 into the patient. FIG. 2C illustrates an exemplary electrical lead 100 exiting delivery system 200 with two electrodes 210, 212 positioned on one side of lead 100, within the mediastinum 202 and facing heart 118. FIG. 2C illustrates the lead 100 advancing in a direction away from sternum 110. This example is not intended to be limiting. For example, the lead 100 may also be advanced in a direction parallel to the sternum 110. In some implementations, delivery system 200 may be configured such that lead 100 advances in the opposite direction, under sternum 110, advances away from sternum 110 at an angle that corresponds to an angle of one or more ribs of patient 104, and/or advances in other orientations. Similarly, an exemplary device as shown in FIG. 2 may be flipped around so that the handle would be on the left side of FIG. 2, or held in other positions by the physician, prior to system actuation and insertion of lead 100.

Distal end 206 of delivery system 200 may be configured to move or puncture tissue during insertion, for example, with a relatively blunt tip (e.g., as described herein), to facilitate entry into the mediastinum without requiring a surgical incision to penetrate through intercostal muscles and other tissues. A blunt access tip, while providing the ability to push through tissue, can be configured to limit the potential for damage to the pericardium or other critical tissues or vessels that the tip may contact.

In an exemplary implementation, the original incision made by the physician above or adjacent to the sternum may also be used to insert a controller, pulse generator or additional electrode to which the implanted lead may be connected.

The delivery system and lead technologies described herein may be especially well suited for the cardiac pacing lead delivery example described above. While this particular application has been described in detail, and may be utilized throughout the descriptions below, it is contemplated that the delivery system(s) 200 and lead(s) 100 herein may be utilized in other procedures as well, such as the insertion of a defibrillation lead.

Figure 3:
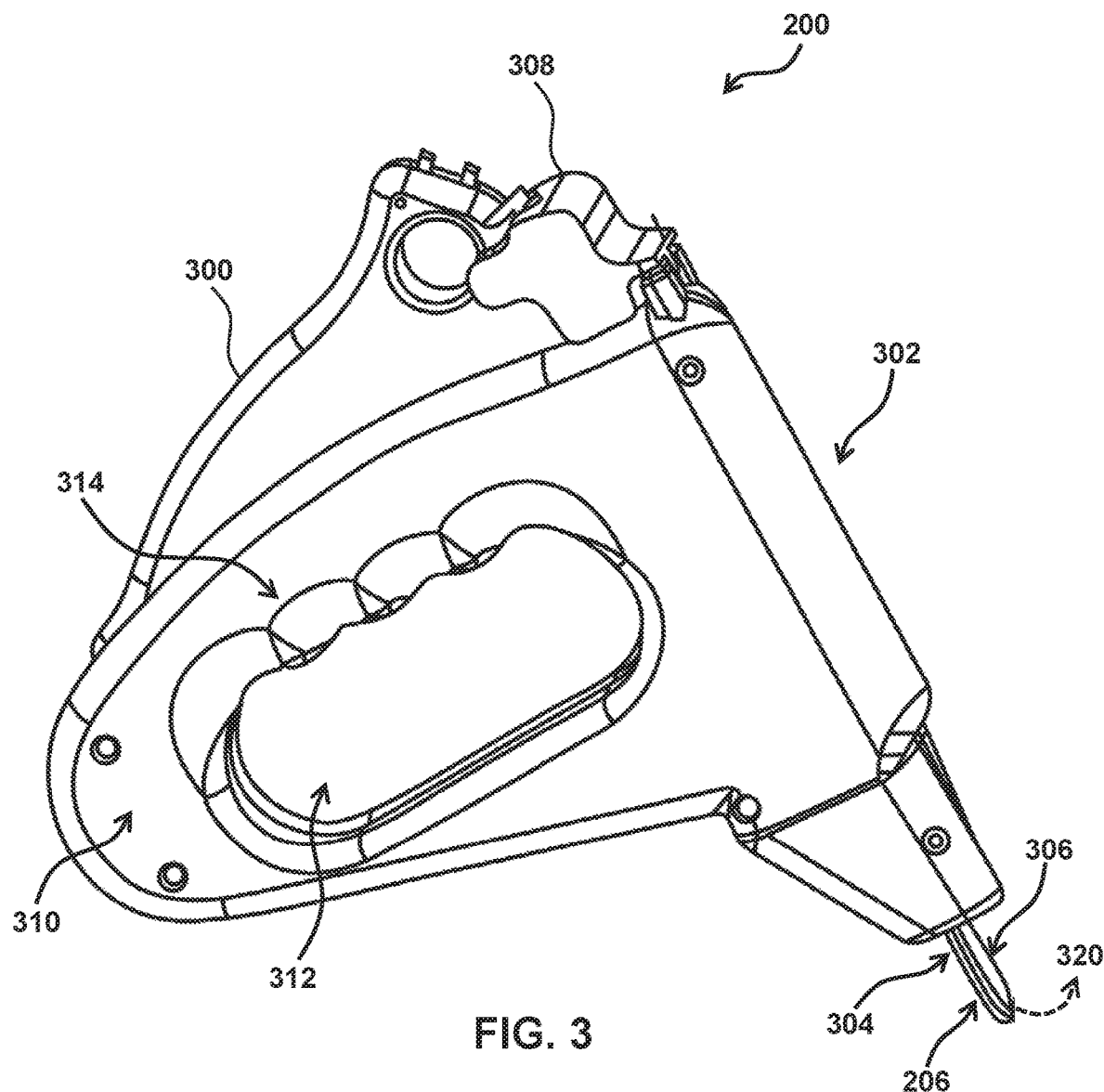
FIG. 3 illustrates an exemplary delivery system, in accordance with certain aspects of the disclosure.

FIG. 3 illustrates an exemplary delivery system 200. Delivery system 200 can include a handle 300, a component advancer 302, a first insertion tip 304, a second insertion tip 306, a lock 308, and/or other components. Handle 300 may be configured to be actuated by an operator. In some implementations, handle 300 may be coupled to a body 310 and/or other components of delivery system 200. Body 310 may include an orifice 312, finger depressions 314, a knurled surface, a lever arm, and/or other components configured to facilitate gripping of handle 300 by an operator. In some implementations, handle 300 and the body of the delivery system 200 may be coated with a material or their surfaces covered with a texture to prevent slippage of the physician's grasp when using delivery system 200.

Component advancer 302 may be coupled to handle 300 and configured to advance a component such as an electrical lead (as one example) into the patient by applying a force to the portion of the component in response to actuation of handle 300 by the operator.

First insertion tip 304 and second insertion tip 306 may be configured to close around a distal tip and/or segment of the component when the component is placed within component advancer 302. In some implementations, closing around a distal segment of the component may include blocking a path between the component and the environment outside delivery system 200. Closing around the distal segment of the component may also prevent the component from being unintentionally deployed and contacting biological tissue while delivery system 200 is being manipulated by the operator.

First insertion tip 304 and second insertion tip 306 may also be configured to fully enclose the distal segment of the component when the component is placed within component advancer 302. Fully enclosing the distal segment of the component may include covering, surrounding, enveloping, and/or otherwise preventing contact between the distal segment of the component and an environment around first insertion tip 304 and second insertion tip 306.

In still other implementations, first insertion tip 304 and second insertion tip 306 may be configured to only partially enclose the distal segment of the component when the component is placed within component advancer 302. For example, first insertion tip 304 and/or second insertion tip 306 may cover, surround, envelop, and/or otherwise prevent contact between one or more portions (e.g., surfaces, ends, edges, etc.) of the distal segment of the component and the environment around tips 304 and 306, but the tips 304 and 306 may also still block the path between the component and the environment outside the delivery system 200 during insertion.

In some implementations, first insertion tip 304 and second insertion tip 306 may be configured such that the component is held within component advancer 302 rather than within first insertion tip 304 and second insertion tip 306, prior to the component being advanced into the patient.

First insertion tip 304 and second insertion tip 306 may be further configured to push through biological tissue when in a closed position and to open (see, e.g., 320 in FIG. 3) to enable the component to exit from the component advancer 302 into the patient. In some implementations, opening may comprise second insertion tip 306 moving away from first insertion tip 304, and/or other opening operations. In some implementations, first and second insertion tips 304, 306 may be configured to open responsive to actuation of handle 300.

In some implementations, first insertion tip 304 and/or second insertion tip 306 may be configured to close (or re-close) after the component exits from the component advancer 302, to facilitate withdrawal of delivery system 200 from the patient. Thus, first insertion tip 304 and second insertion tip 306 may be configured to move, after the component exits from component advancer 302 into the patient, to a withdrawal position to facilitate withdrawal of first insertion tip 304 and second insertion tip 306 from the biological tissue. In some implementations, the withdrawal position may be similar to and/or the same as an original closed position. In some implementations, the withdrawal position may be a different position. In some implementations, the withdrawal position may be wider than the closed position, but narrower than an open position. For example, first insertion tip 304 and/or second insertion tip 306 may move to the open position to release the component, but then move to a different position with a narrower profile (e.g., the withdrawal position) so that when the tips 304, 306 are removed they are not met with resistance pulling through a narrow rib space, and/or other biological tissue.

In some implementations, first and second insertion tips 304, 306 may have blunt edges. Blunt edges may include rounded and/or otherwise dull edges, corners, surfaces, and/or other components of first and second insertion tips 304, 306. The blunt edges may be configured to prevent insertion tips 304 and 306 from rupturing any veins or arteries, the pericardial sac, the pleura of the lungs, and/or causing any other unintentional damage to biological tissue. The blunt edges may prevent, for example, rupturing veins and/or arteries by pushing these vascular items to the side during insertion. The blunt edges may also prevent, for example, the rupturing of the pericardium or pleura because they are not sharp.

Figure 4:
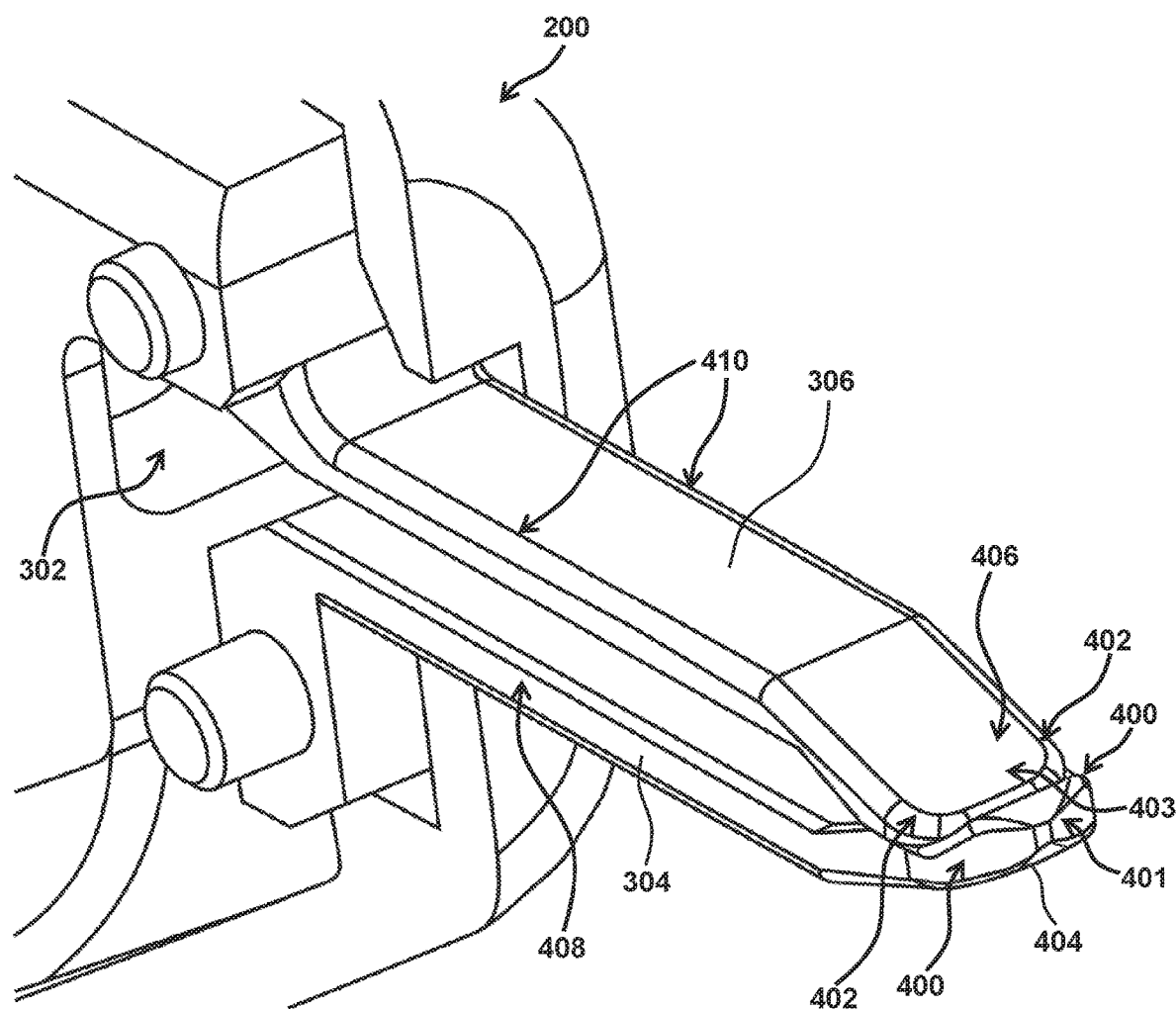
FIG. 4 illustrates an example of first and second insertion tips of the delivery system with blunt edges, in accordance with certain aspects of the disclosure.

FIG. 4 illustrates first and second insertion tips 304, 306 with exemplary implementations of such blunt edges. As shown in FIG. 4, first and second insertion tips 304, 306 may have rounded corners 400, 402 and/or end surfaces 401, 403 at their respective ends 404, 406. First and second insertion tips 304, 306 may have rounded edges 408, 410 that run along a longitudinal axis of tips 304, 306. However, this description is not intended to be limiting. In some implementations, first and second insertion tips 304, 306 may also have sharp edges, ends, and/or other features.

Figure 5:
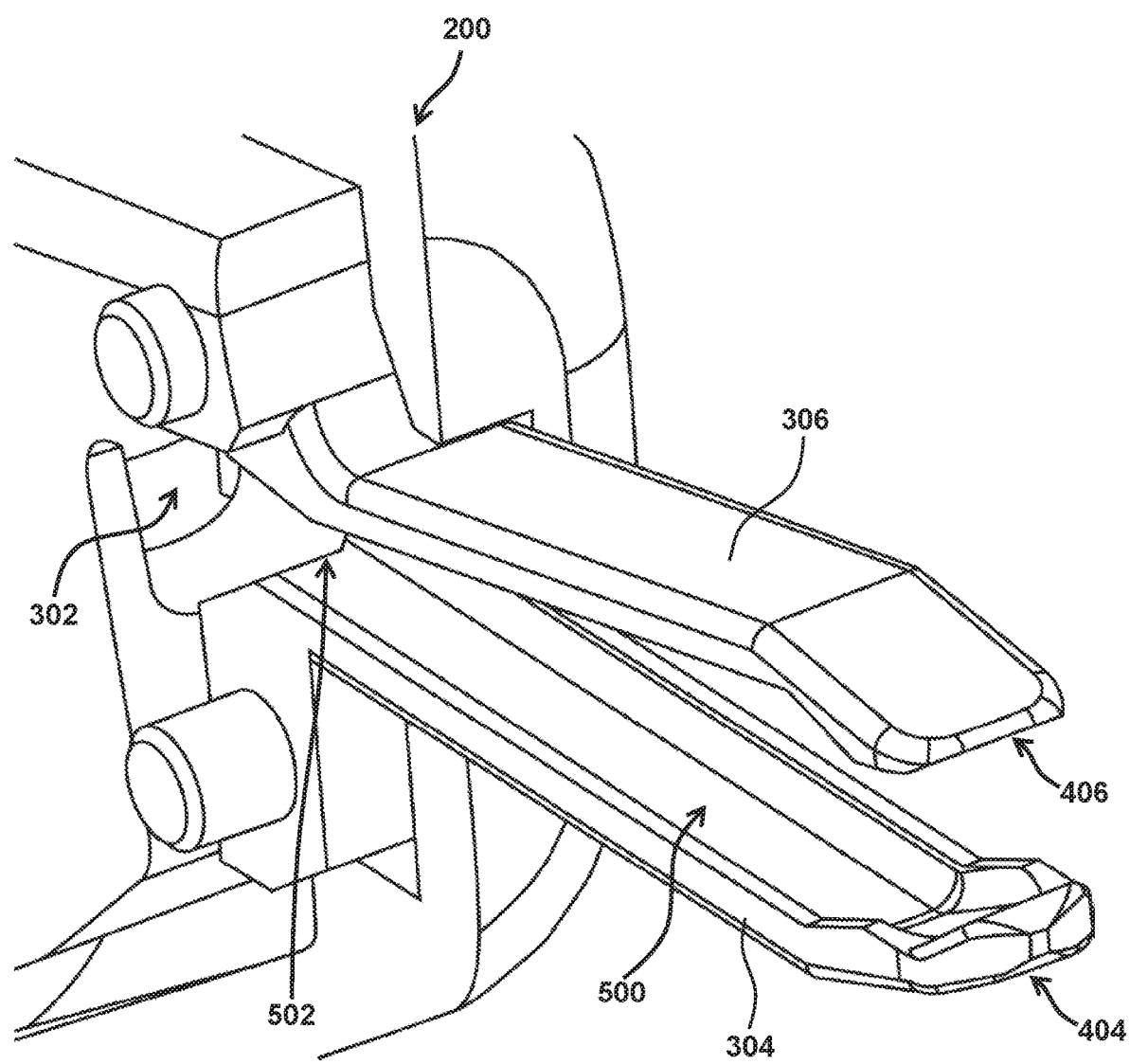
FIG. 5 illustrates an exemplary channel at least partially complimentary to a shape of the component and configured to guide the component into the patient, in accordance with certain aspects of the disclosure.

In some implementations, first and second insertion tips 304, 306 may each include a channel at least partially complimentary to a shape of the component and configured to guide the component into the patient. FIG. 5 illustrates an example of such a channel. As shown in FIG. 5, first insertion tip 304 may include a channel 500 at least partially complimentary to a shape of the component and configured to guide the component into the patient. Second insertion tip 306 may also include a channel similar to and/or the same as channel 500 (although the channel in insertion tip 306 is not visible in FIG. 5). Channel 500 may extend along a longitudinal axis of insertion tip 304 from an end 502 of insertion tip 304 configured to couple with component advancer 302 toward end 404.

In some implementations, channel 500 may be formed by a hollow area of insertion tip 304 that forms a trench, for example. The hollow area and/or trench may have one or more shapes and/or dimensions that are at least partially complimentary to a shape and/or dimension(s) of the component, and are configured to guide the component into the patient. In some implementations, the hollow area and/or trench may be configured such that the component may only slide within channel 500 inside the insertion tips 304, 306, and therefore prevent the component from advancing out one of the sides of the insertion tips 304, 306 when pushed by component advancer 302.

In some implementations, channel 500 may include a second channel and/or groove configured to engage alignment features included on a component. The second channel or groove may be located within channel 500, but be deeper and/or narrower than channel 500. The component may then include a rib and/or other alignment features configured to engage such a groove. The rib may be on an opposite side of the component relative to electrodes, for example. These features may enhance the guidance of a component through channel 500, facilitate alignment of a component in channel 500 (e.g., such that the electrodes are oriented in a specific direction in tips 304, 306, preventing the component from exiting tips 304, 306 to one side or the other (as opposed to exiting out ends 404, 406), and/or have other functionalities.

In some implementations, the second channel and/or groove may be sized to be just large enough to fit an alignment feature of the component within the second channel and/or groove. This may prevent an operator from pulling a component too far up into delivery system 200 (FIG. 3) when loading delivery system 200 with a component (e.g., as described below).

The channels and/or grooves may also provide a clinical benefit. For example, the channel and/or groove may allow for narrower insertion tips 304 and 306 that need not be configured to surround or envelop all sides of the component (e.g., they may not need sidewalls to keep the component in position during implantation). If surrounding or enveloping all sides of a component is necessary, the insertion tips would need to be larger, and would meet with greater resistance when separating tissue planes within intercostal spaces, for example. However, in other implementations (e.g., as described herein), insertion tips 304, 306 may completely surround and/or envelop the component.

Figure 6:
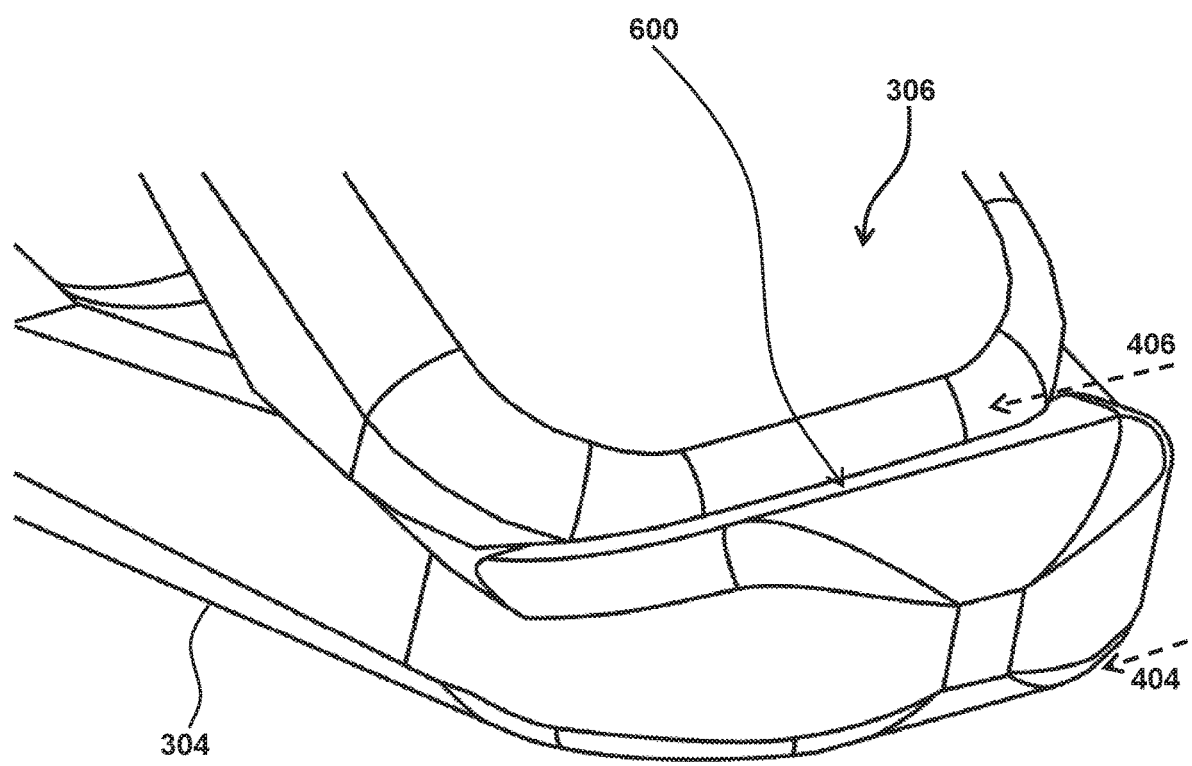
FIG. 6 illustrates a first insertion tip being longer than a second insertion tip, in accordance with certain aspects of the disclosure.

In some implementations, as shown in FIG. 6, a first insertion tip 304 may be longer than a second insertion tip 306 and the end 404 of first insertion tip 304 will extend beyond the end 406 of insertion tip 306. Such a configuration may assist with spreading of tissue planes and help to avoid pinching tissue, veins, arteries or the like while delivery system 200 is being manipulated through biological tissue.

In some implementations, both the first and second insertion tips 304, 306 may be moveable. In other implementations, the first insertion tip 304 may be fixed, and second insertion tip 306 may be moveable.

In one particular implementation, a fixed insertion tip 304 may be longer than a movable insertion tip 306. This configuration may allow more pressure to be exerted on the outermost edge (e.g., end 404 of tip 304) of delivery system 200 without (or with reduced) concern that tips 304 and 306 will open when pushing through biological tissue. Additionally, the distal ends 404 and 406 may form an underbite 600 that allows distal end 406 of movable insertion tip 306 (in this example) to seat behind fixed insertion tip 304, and thus prevent tip 406 from experiencing forces that may inadvertently open movable insertion tip 306 during advancement. However, this description is not intended to be limiting. In some implementations, a movable insertion tip 306 may be longer than a fixed insertion tip 304.

Figure 7:
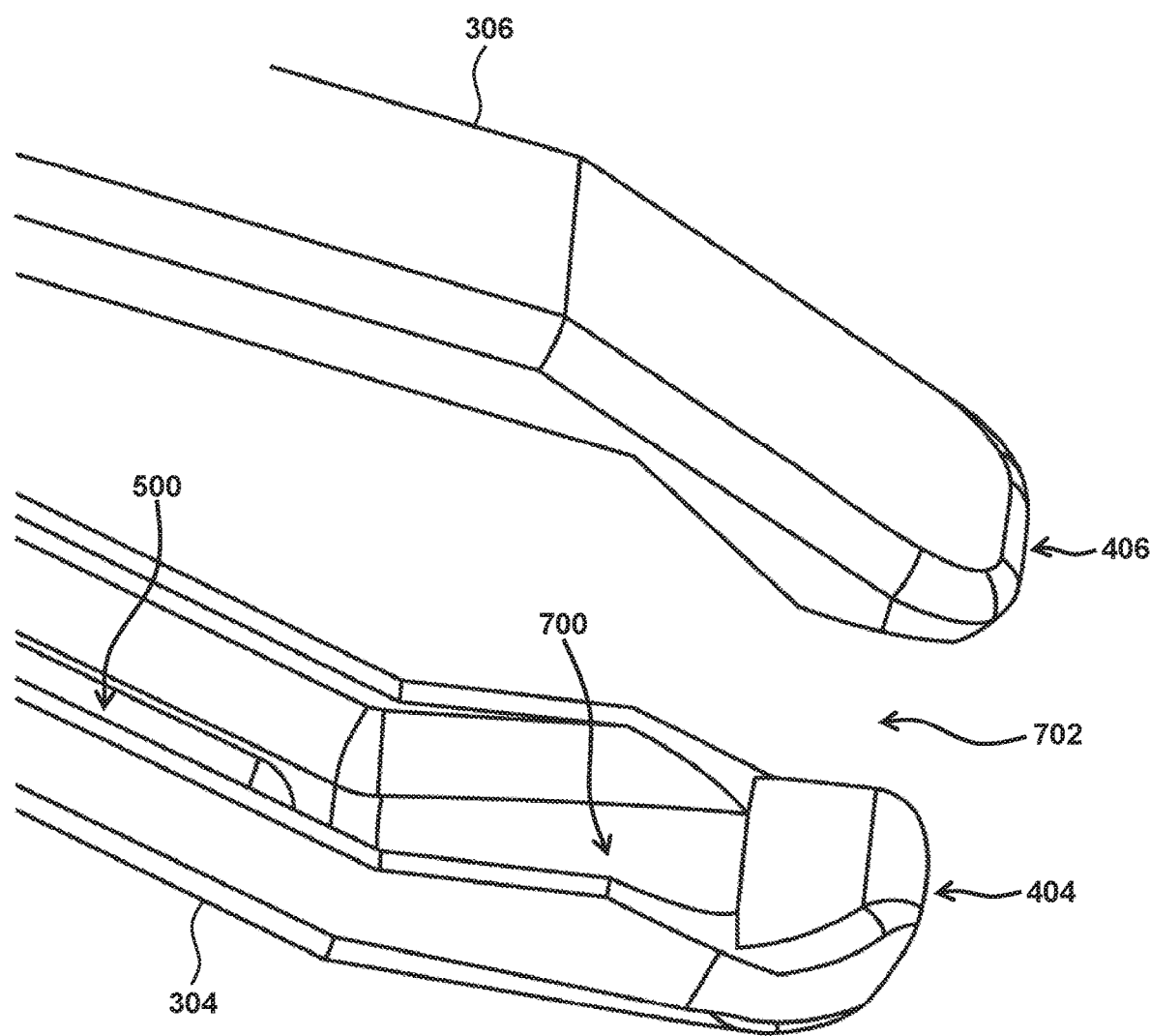
FIG. 7 illustrates an example of a ramped portion of an insertion tip, in accordance with certain aspects of the disclosure.

In some implementations, a fixed (e.g., and/or longer) insertion tip 304 may include a ramped portion configured to facilitate advancement of the component into the patient in a particular direction. FIG. 7 illustrates an example of a ramped portion 700 of insertion tip 304. Ramped portion 700 may be located on an interior surface 702 of insertion tip 304, between channel 500 and distal end 404 of insertion tip 304. Ramped portion 700 may be configured to facilitate advancement of the component into the patient in a particular direction. The particular direction may be a lateral direction relative to a position of insertion tip 304, for example. The lateral deployment of a component (e.g., an electrical lead) when it exits insertion tip 304 and moves into the anterior mediastinum of the patient may facilitate deployment without contacting the heart (e.g., as described relative to FIGS. 2A-2C above). Ramped portion 700 may also encourage the component to follow a preformed bias (described below) and help prevent the lead from deploying in an unintentional direction.

Figure 8:
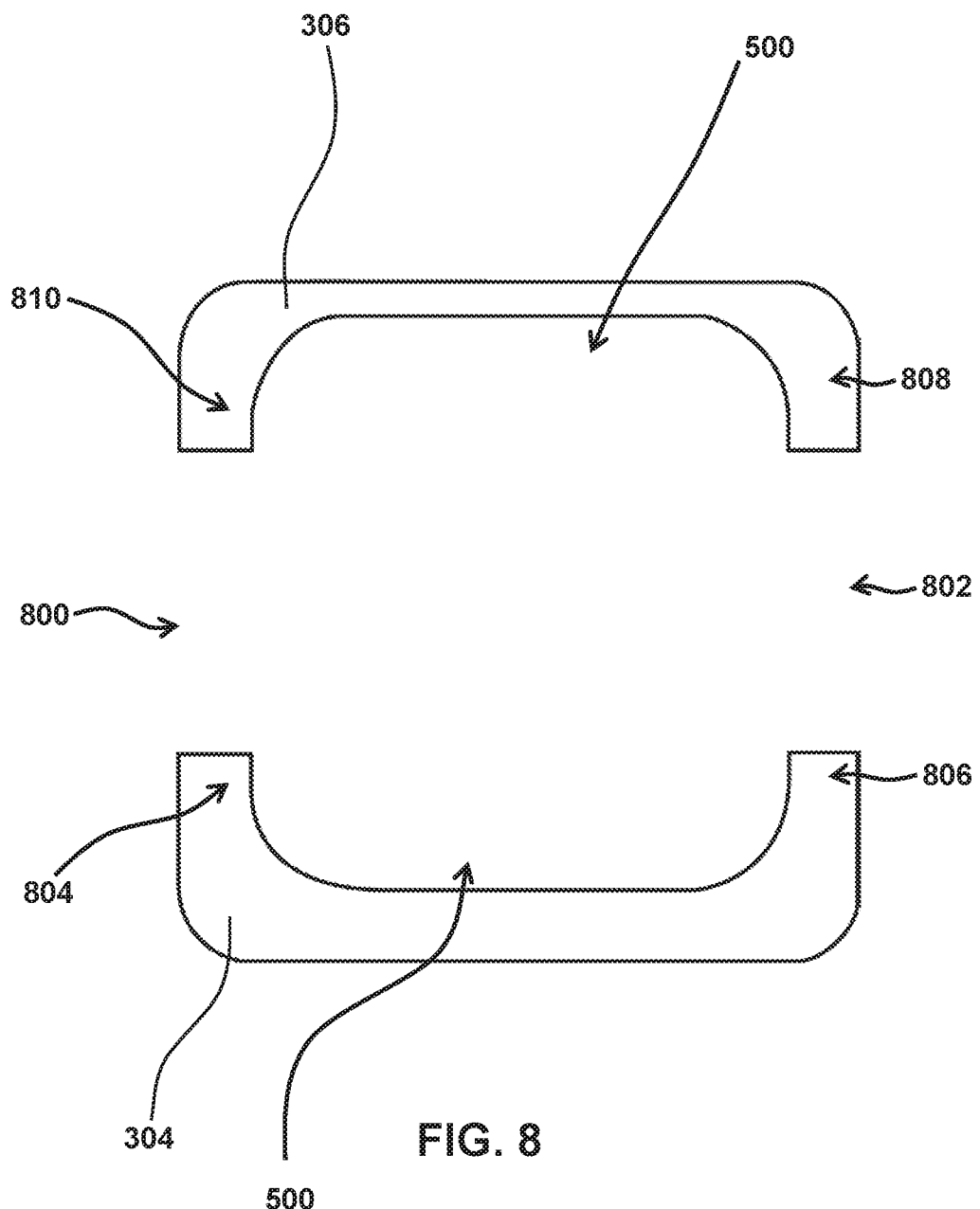
FIG. 8 illustrates an example of insertion tips with open side walls, in accordance with certain aspects of the disclosure.

In some implementations, insertion tips 304, 306 may have open side walls. FIG. 8 illustrates an example of insertion tips 304, 306 with open side walls 800, 802. FIG. 8 illustrates a cross sectional view of insertion tips 304, 306, looking at insertion tips 304, 306 from distal ends 404, 406 (as shown in FIG. 7). Open side walls 800, 802 may be formed by spaces between insertion tip 304 and insertion tip 306. In the example of FIG. 8, insertion tips 304 and 306 are substantially "U" shaped, with the ends 804, 806, 808, 810 extending toward each other, but not touching, such that open side walls 800 and 802 may be formed. Open side walls 800, 802 may facilitate the use of a larger component (e.g., a component that does not fit within channel(s) 500), without having to increase a size (e.g., a width, etc.) of insertion tips 304, 306. This may avoid effects larger insertion tips may have on biological tissue. For example, larger insertion tips are more invasive than smaller insertion tips. As such, larger insertion tips may meet with greater resistance when separating tissue planes within intercostal spaces during deployment and may cause increased trauma than insertion tips having a reduced cross sectional size.

Figure 9A:
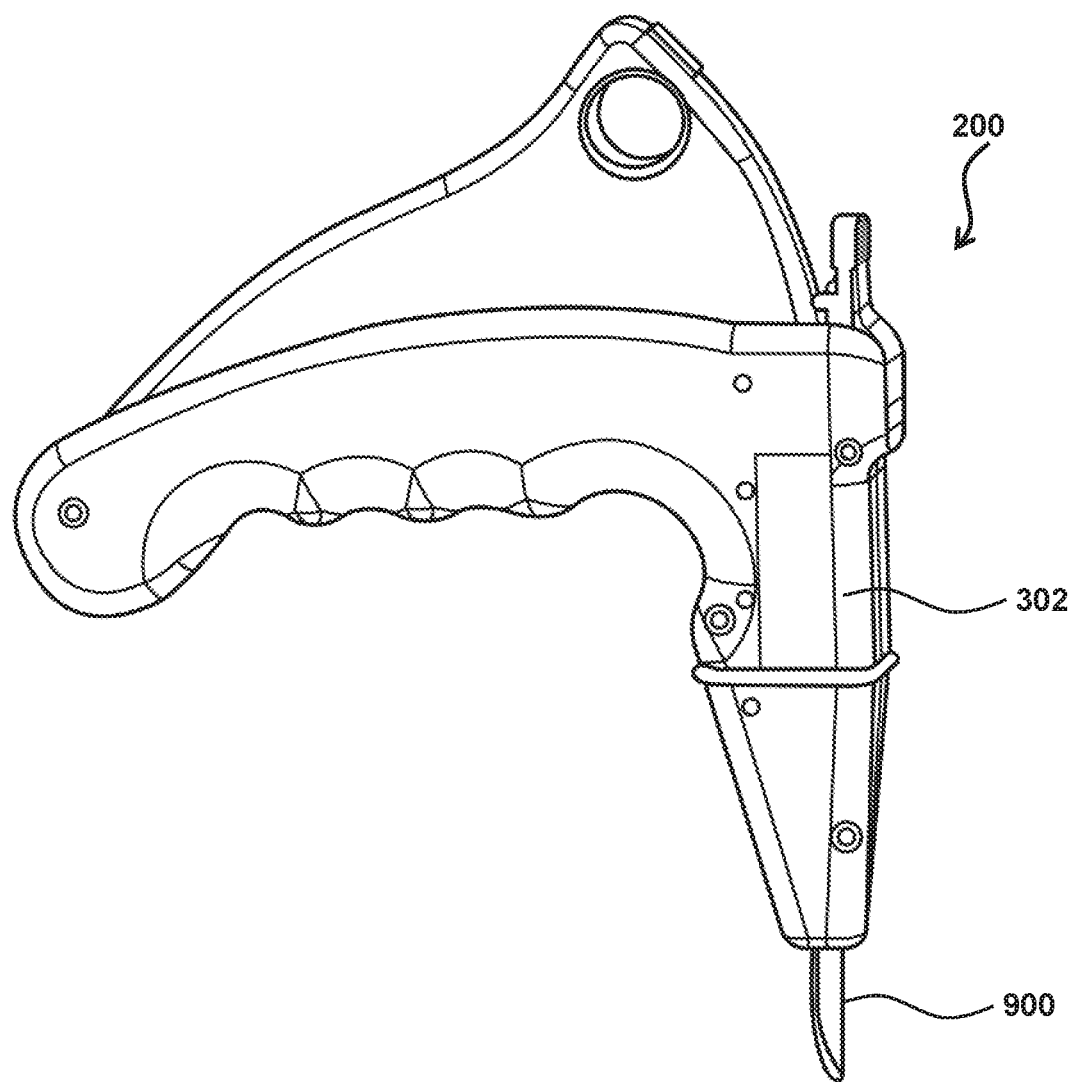
FIG. 9A illustrates one possible example of a delivery system having a unitary insertion tip, in accordance with certain aspects of the disclosure.

In some implementations, delivery system 200 (FIG. 3) may include a handle 300 (FIG. 3), a component advancer 302 (FIG. 3), and a unitary insertion tip (e.g., instead of first and second insertion tips 304 and 306). FIG. 9A illustrates one possible example of a delivery system 200 having a unitary insertion tip 900. Insertion tip 900 may be coupled to a component advancer 302 similar to and/or in the same manner that insertion tips 304 and 306 (FIG. 7) may be coupled to component advancer 302.

Figure 9B:
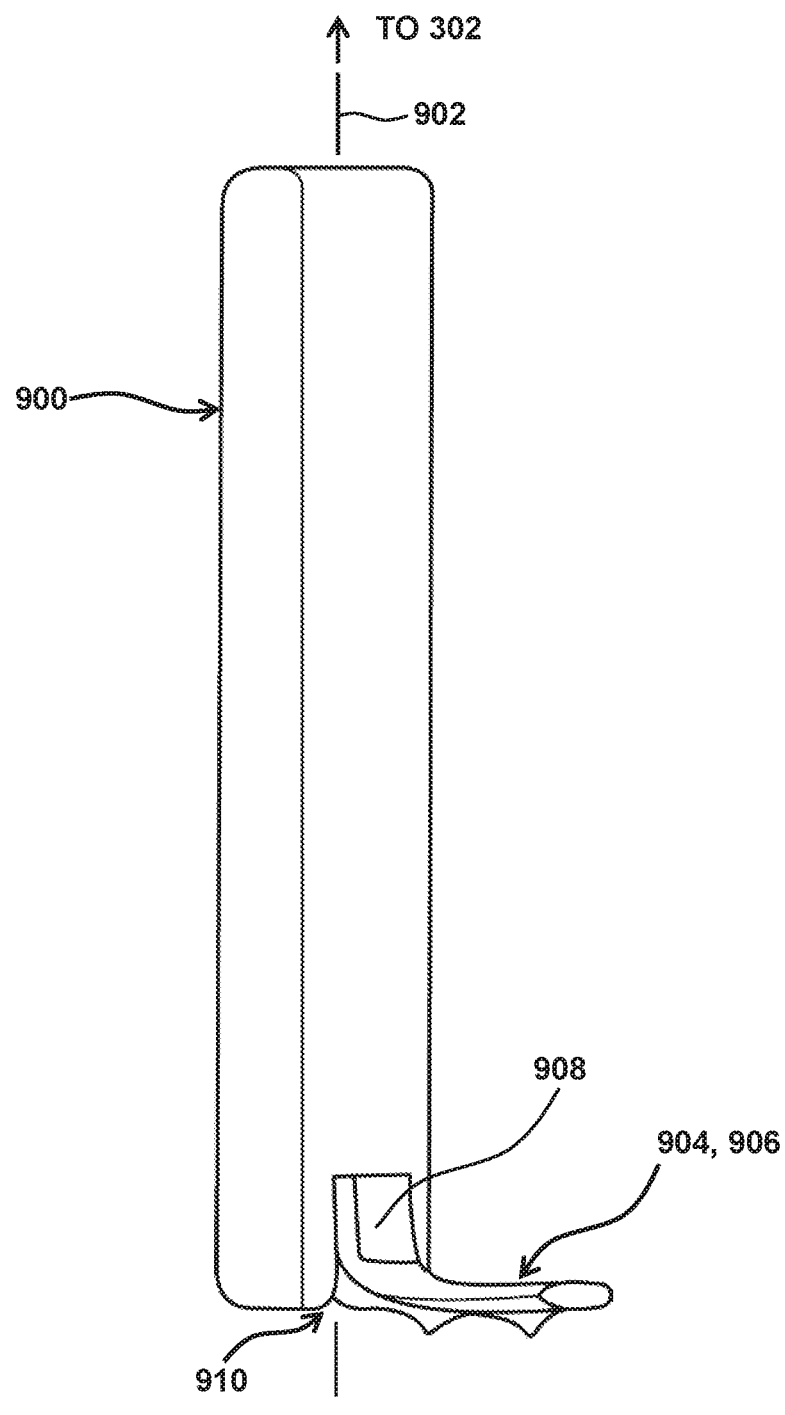
FIG. 9B illustrates one possible example of a unitary insertion tip, in accordance with certain aspects of the disclosure.

Unitary insertion tip 900 may have a circular, rectangular, wedge, square, and/or other cross sectional shape(s). In some implementations, insertion tip 900 may form a (circular or rectangular, etc.) tube extending along a longitudinal axis 902 (FIG. 9B) of insertion tip 900. Referring to FIG. 9B, in some implementations, insertion tip 900 may be configured to hold the component (labeled as 904) when the component is placed within component advancer 302. In some implementations, insertion tip 900 may be configured to hold a distal end (labeled as 906) and/or tip of component 904 when component 904 is placed within component advancer 302.

Insertion tip 900 may be configured to push through biological tissue and may include a distal orifice 908 configured to enable component 904 to exit from component advancer 302 into the patient.

Figure 9C:
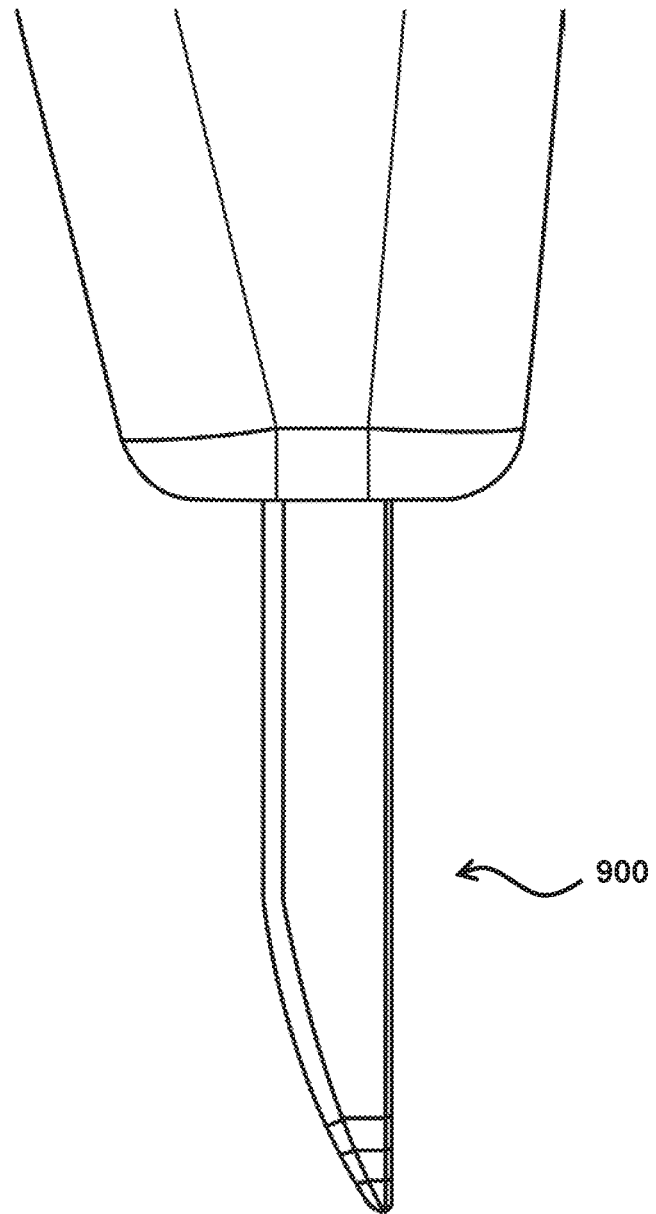
FIG. 9C illustrates an alternative insertion tip design having a wedge shape, in accordance with certain aspects of the disclosure.

FIG. 9C illustrates an alternative insertion tip 900 design having a wedge shape. A wedge-shaped insertion tip 900 reduces and/or eliminates the exposure of distal orifice 908 to the surrounding tissue during insertion. This design prevents tissue coring since only the leading edge of insertion tip 900 is exposed and thereby separates tissues rather than coring or cutting tissue during insertion. Accordingly, the present disclosure contemplates an insertion tip that may be configured to reduce the exposure of the distal orifice during insertion.

Figure 9D:
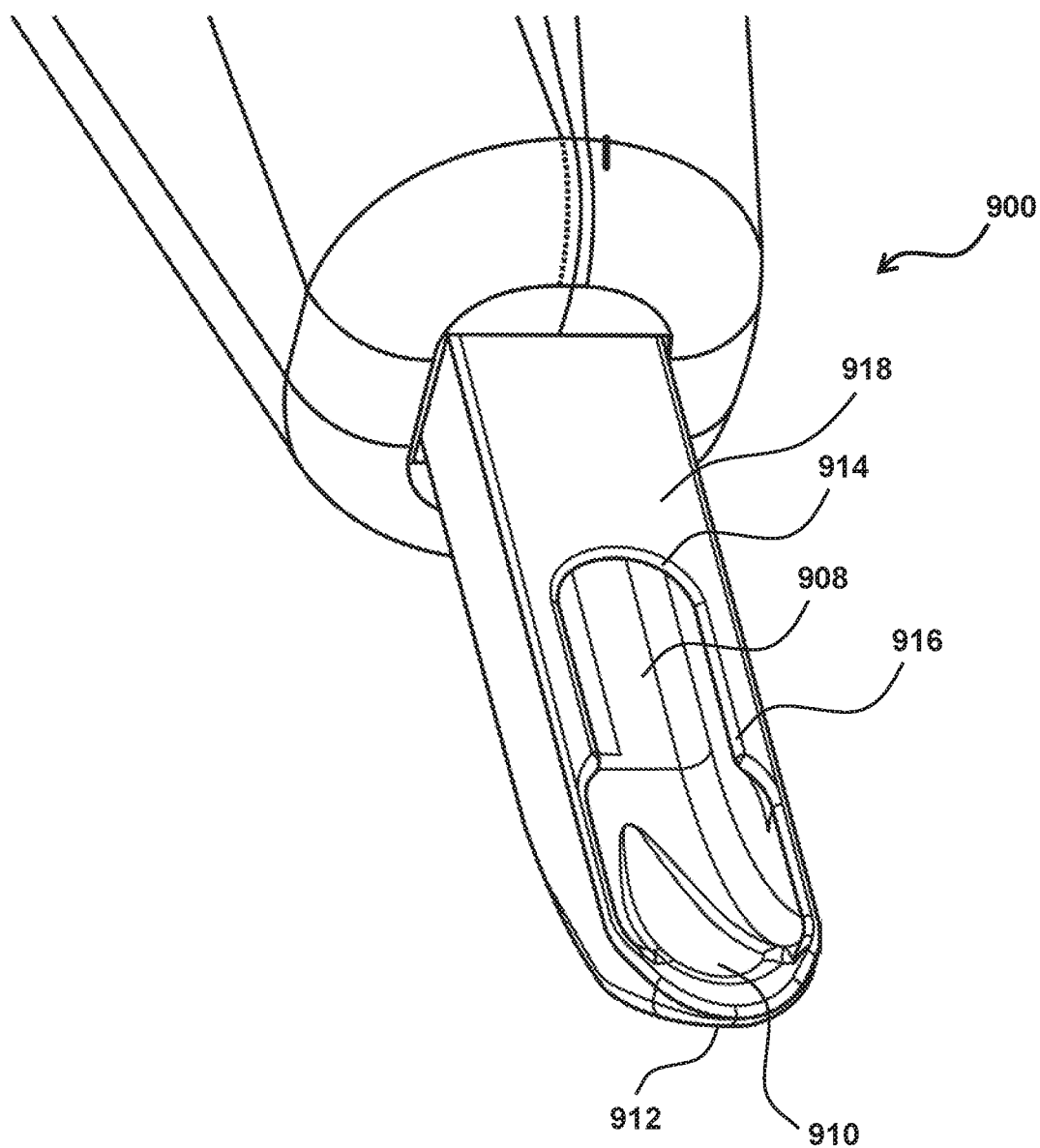
FIG. 9D illustrates certain features applicable to a unitary insertion tip design, in accordance with certain aspects of the disclosure.

Referring to FIG. 9D, distal tip 912 may be rounded into an arc so the deployment force exerted by the physician during insertion concentrates in a smaller area (the distalmost portion of distal tip 912). Additionally, the distalmost portion of distal tip 912 may be blunted to minimize trauma and damage to surrounding tissue during insertion. Notch 914 provides additional room for the proximal end of lead 100 having a rigid electrical connector to more easily be inserted when loading lead 100 in delivery system 200. Rails 916 overlap lead 100 and hold lead 100 flat when the lead is retracted and held within delivery system 200. In some implementations, the inner edge of rails 916 gradually widen as rails 916 advance toward distal tip 912.

FIG. 9D illustrates certain features applicable to a unitary insertion tip design.

In some implementations, insertion tip 900 may include a movable cover 918 configured to prevent the biological tissue from entering distal orifice 908 when insertion tip 900 pushes through the biological tissue. The moveable cover may move to facilitate advancement of component 904 into the patient.

It is contemplated that many of the other technologies disclosed herein can also be used with the unitary tip design. For example, insertion tip 900 may include a ramped portion 910 configured to facilitate advancement of the component into the patient in a particular direction and to allow the protruding electrodes 210, 212 to pass easier through the channel created within insertion tip 900.

In some implementations, delivery system 200 (FIG. 3) may include a dilator. In some implementations, insertion tips 304, 306, and/or insertion tip 900 may operate in conjunction with such a dilator. Use of a dilator may allow an initial incision to be smaller than it may otherwise be. The dilator may be directionally oriented to facilitate insertion of a component (e.g., an electrical lead) through the positioned dilator manually, and/or by other means. The dilator may comprise a mechanism that separates first and second insertion tips 304, 306. For example, relatively thin first and second insertion tips 304, 306 may be advanced through biological tissue. An actuator (e.g., a handle, and/or a device couple to the handle operated by the user) may insert a hollow, dilating wedge that separates first and second insertion tips 304, 306. The actuator (operated by the user) may advance a lead through the hollow dilator into the biological tissue. The dilator may also be used to separate the first and second insertion tips 304, 306 such that they lock into an open position. The dilator can then be removed and the lead advanced into the biological tissue.

Figure 10:
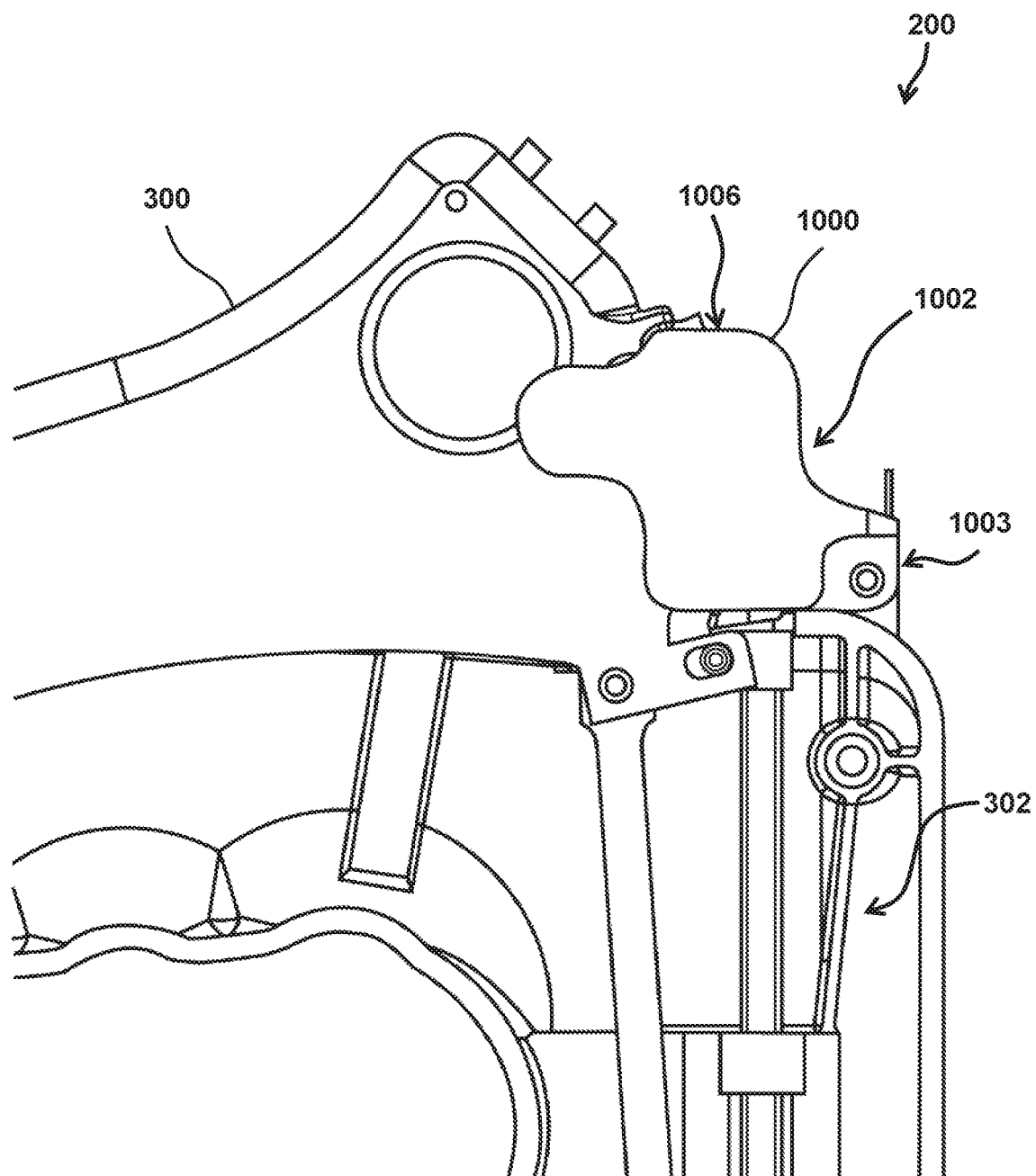
FIG. 10 illustrates an exemplary lock for a delivery system, in a locked position, in accordance with certain aspects of the disclosure.
Figure 11:
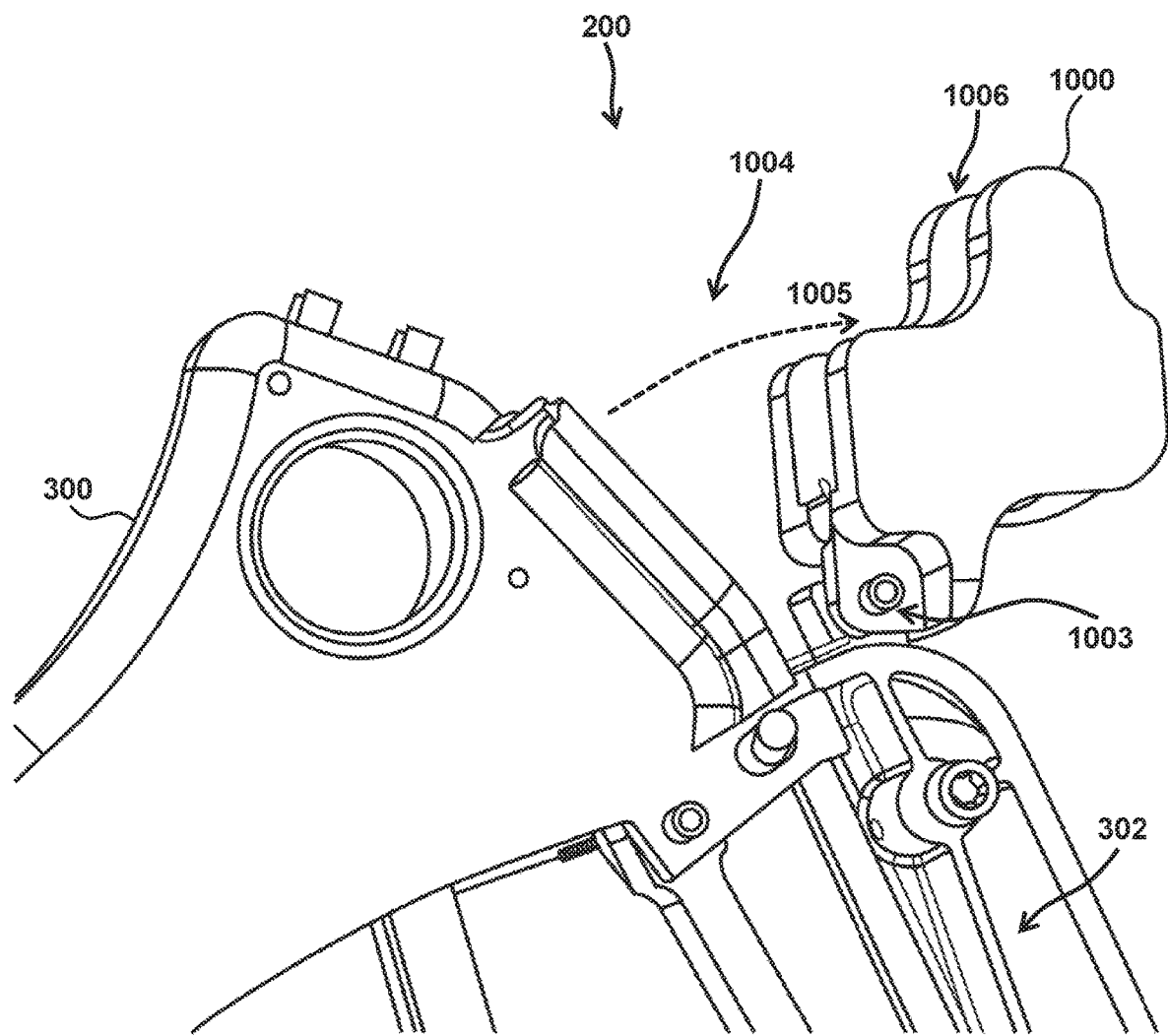
FIG. 11 illustrates the lock in an unlocked position, in accordance with certain aspects of the disclosure.

FIGS. 10 and 11 illustrate an exemplary lock 1000 that may be included in delivery system 200. A lock 1000 may be similar to and/or the same as lock 308 shown in FIG. 3. In some implementations, lock 1000 may be configured to be moved between an unlocked position that allows actuation of handle 300 (and in turn component advancer 302) by the operator and a locked position that prevents actuation, and prevents first insertion tip 304 (FIG. 7) and second insertion 306 tip (FIG. 7) from opening.

FIG. 10 illustrates lock 1000 in a locked position 1002. FIG. 11 illustrates lock 1000 in an unlocked position 1004. Lock 1000 may be coupled to handle 300 and/or component advancer 302 via a hinge 1003 and/or other coupling mechanisms. In some implementations, lock 1000 may be moved from locked position 1002 to unlocked position 1004, and vice versa, by rotating and/or otherwise moving an end 1006 of lock 1000 away from handle 300 (see, e.g., 1005 in FIG. 11). Lock 1000 may be moved from locked position 1002 to unlocked position 1004, and vice versa, by the operator with thumb pressure, trigger activation (button/lever, etc.) for example, and/or other movements. Additionally, the mechanism may also include a safety switch such that a trigger mechanism must be deployed prior to unlocking the lock with the operator's thumb.

When lock 1000 is engaged or in locked position 1002, lock 1000 may prevent an operator from inadvertently squeezing handle 300 to deploy the component. Lock 1000 may prevent the (1) spreading of the distal tips 304, 306, and/or (2) deployment of a component while delivery system 200 is being inserted through the intercostal muscles.

Lock 1000 may be configured such that deployment of the component may occur only when lock 1000 is disengaged (e.g., in the unlocked position 1004 shown in FIG. 11). Deployment may be prevented, for example, while an operator is using insertion tips 304, 306 of delivery system 200 to slide between planes of tissue in the intercostal space as pressure is applied to delivery system 200. Lock 1000 may be configured such that, only once system 200 is fully inserted into the patient can lock 1000 be moved so that handle 300 may be actuated to deliver the component through the spread (e.g., open) insertion tips 304, 306. It should be noted that the specific design of lock 1000 shown in FIGS. 10 and 11 is not intended to be limiting. Other locking mechanism designs are contemplated. For example, the lock 1000 may be designed so that lock 1000 must be fully unlocked to allow the handle 300 to be deployed. A partial unlocking of lock 1000 maintains the handle in the locked position as a safety mechanism. Furthermore, the lock 1000 may be configured such that any movement from its fully unlocked position will relock the handle 300.

Returning to FIG. 3, component advancer 302 may be configured to advance a component into a patient. The component may be an electrical lead (e.g., as described herein), and/or other components.

The component advancer 302 may be configured to removably engage a portion of the component, and/or to deliver the component into the patient through insertion tips 304 and 306. In some implementations, component advancer 302 and/or other components of system 200 may include leveraging components configured to provide a mechanical advantage or a mechanical disadvantage to an operator such that actuation of handle 300 by the operator makes advancing the component into the patient easier or more difficult. For example, the leveraging components may be configured such that a small and/or relatively light actuation pressure on handle 300 causes a large movement of a component (e.g., full deployment) from component advancer 302. Or, in contrast, the leveraging components may be configured such that a strong and/or relatively intense actuation pressure is required to deliver the component. In some implementations, the leveraging components may include levers, hinges, wedges, gears, and/or other leveraging components (e.g., as described herein). In some implementations, handle 300 may be advanced in order to build up torque onto component advancer 302, without moving the component. Once sufficient torque has built up within the component advancer, the mechanism triggers the release of the stored torque onto the component advancer, deploying the component.

In some implementations, component advancer 302 may include a rack and pinion system coupled to handle 300 and configured to grip the component such that actuation of handle 300 by the operator causes movement of the component via the rack and pinion system to advance the component into the patient. In some implementations, the rack and pinion system may be configured such that movement of handle 300 moves a single or dual rack including gears configured to engage and rotate a single pinion or multiple pinions that engage the component, so that when the single pinion or multiple pinions rotate, force is exerted on the component to advance the component into the patient.

Figure 12A:
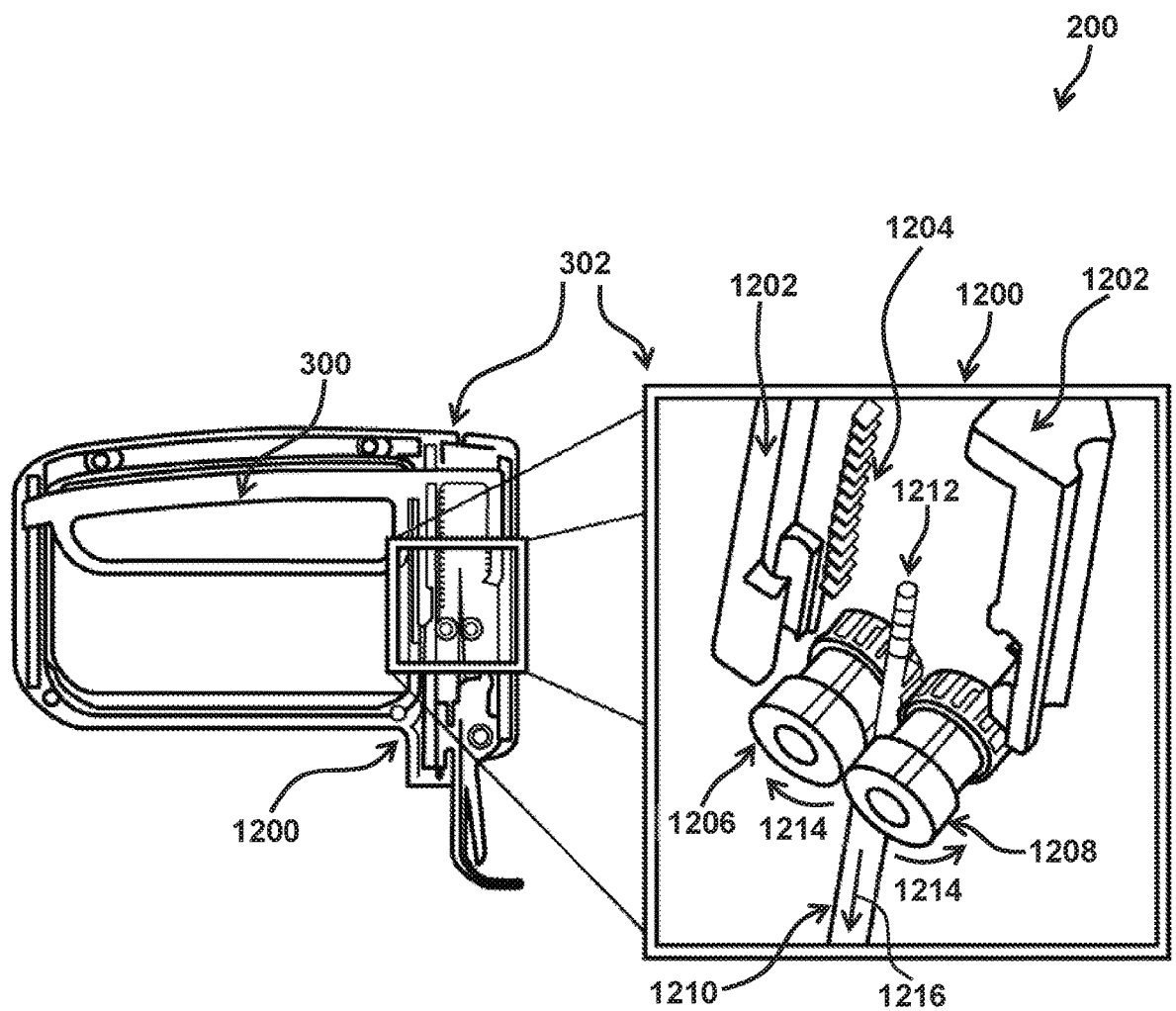
FIG. 12A illustrates an example rack and pinion system that may be included in a component advancer of the delivery system, in accordance with certain aspects of the disclosure.

FIG. 12A illustrates an exemplary rack and pinion system 1200. Rack and pinion system may include rack(s) 1202 with gears 1204. Example system 1200 includes two pinions 1206, 1208. Pinions 1206 and 1208 may be configured to couple with a component 1210 (e.g., an electrical lead), at or near a distal end 1212 of component 1210, as shown in FIG. 12A. Rack and pinion system 1200 may be configured such that movement of handle 300 moves rack 1202 comprising gears 1204 configured to engage and rotate pinions 1206, 1208 that engage component 1210, so that when pinions 1206, 1208 rotate 1214, force is exerted 1216 on component 1210 to advance component 1210 into the patient.

Figure 12B:
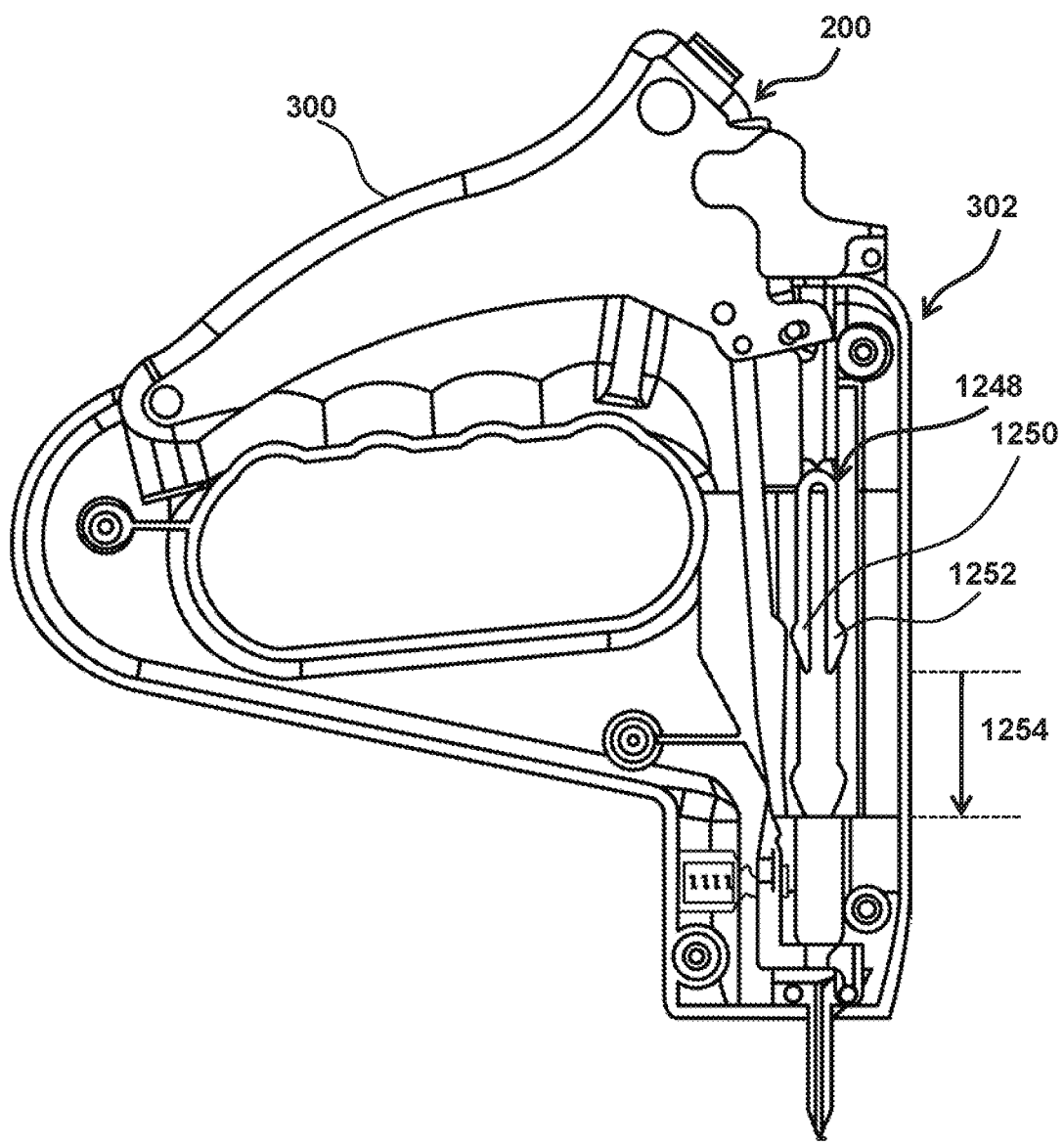
FIG. 12B illustrates an example clamp system that may be included in a component advancer of the delivery system, in accordance with certain aspects of the disclosure.

In some implementations, responsive to handle 300 being actuated, a component (e.g., component 1210) may be gripped around a length of a body of the component, as shown in FIG. 12B. The body of the component may be gripped by two opposing portions 1250, 1252 of component advancer 302 that engage either side of the component, by two opposing portions that engage around an entire circumferential length of a portion of the body, and/or by other gripping mechanisms.

Once gripped, further actuation of handle 300 may force the two opposing portions within component advancer 302 to traverse toward a patient through delivery system 200. Because the component may be secured by these two opposing portions, the component may be pushed out of delivery system 200 and into the (e.g., anterior mediastinum) of the patient. By way of a non-limiting example, component advancer 302 may comprise a clamp 1248 having a first side 1250 and a second side 1252 configured to engage a portion of the component. Clamp 1248 may be coupled to handle 300 such that actuation of handle 300 by the operator may cause movement of the first side 1250 and second side 1252 of clamp 1248 to push on the portion of the component to advance the component into the patient. Upon advancing the component a fixed distance (e.g., distance 1254) into the patient, clamp 1248 may release the component. Other gripping mechanisms are also contemplated.

Returning to FIG. 3, in some implementations, component advancer 302 may include a pusher tube coupled with handle 300 such that actuation of handle 300 by the operator causes movement of the pusher tube to push on the portion of the component to advance the component into the patient. In some implementations, the pusher tube may be a hypo tube, and/or other tubes. In some implementations, the hypo tube may be stainless steel and/or be formed from other materials. However, these examples are not intended to be limiting. The pusher tube may be any tube that allows system 200 to function as described herein.

Figure 13:
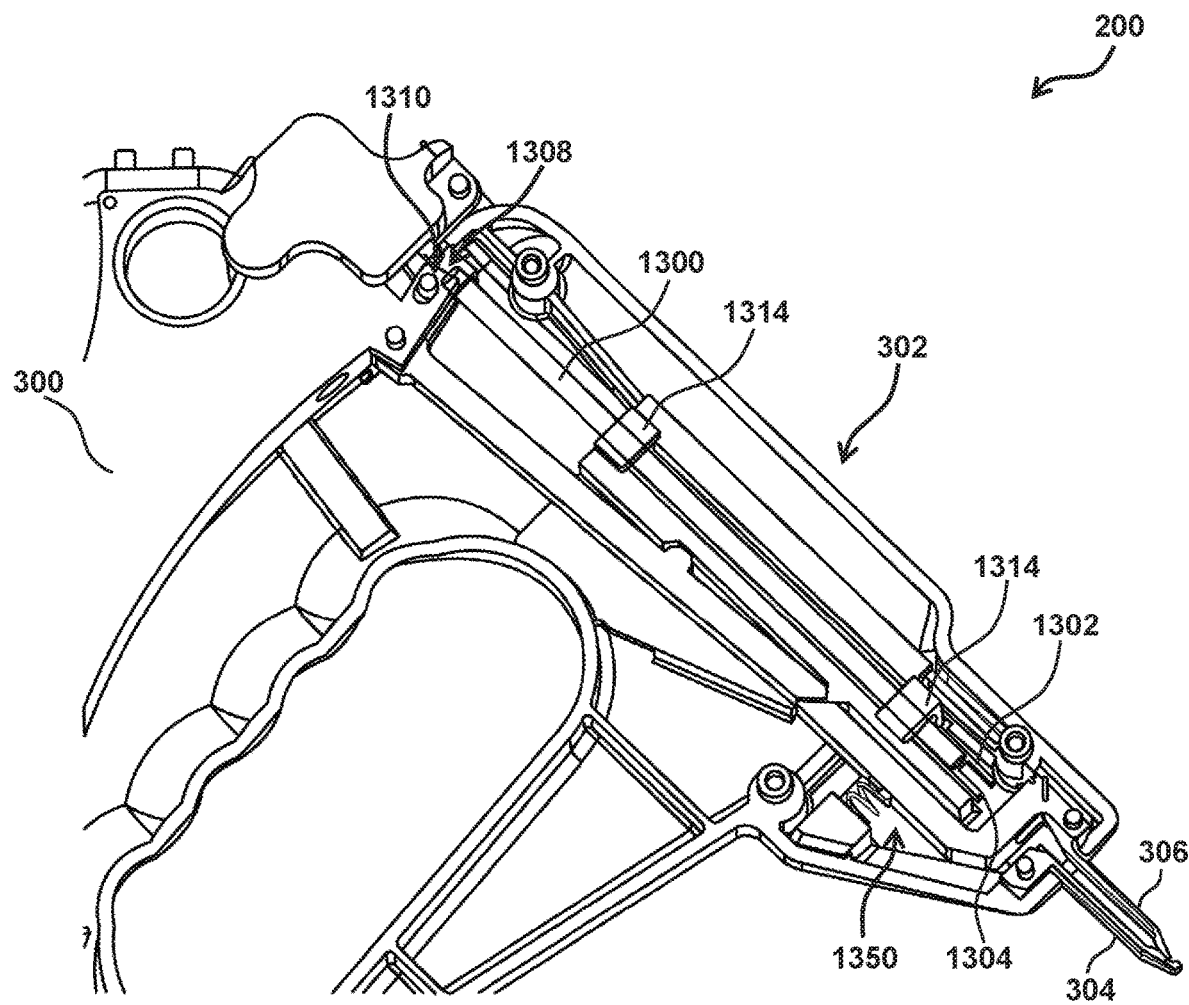
FIG. 13 illustrates a view of an exemplary implementation of a component advancer including a pusher tube coupled with the handle of a delivery system, in accordance with certain aspects of the disclosure.
Figure 14:
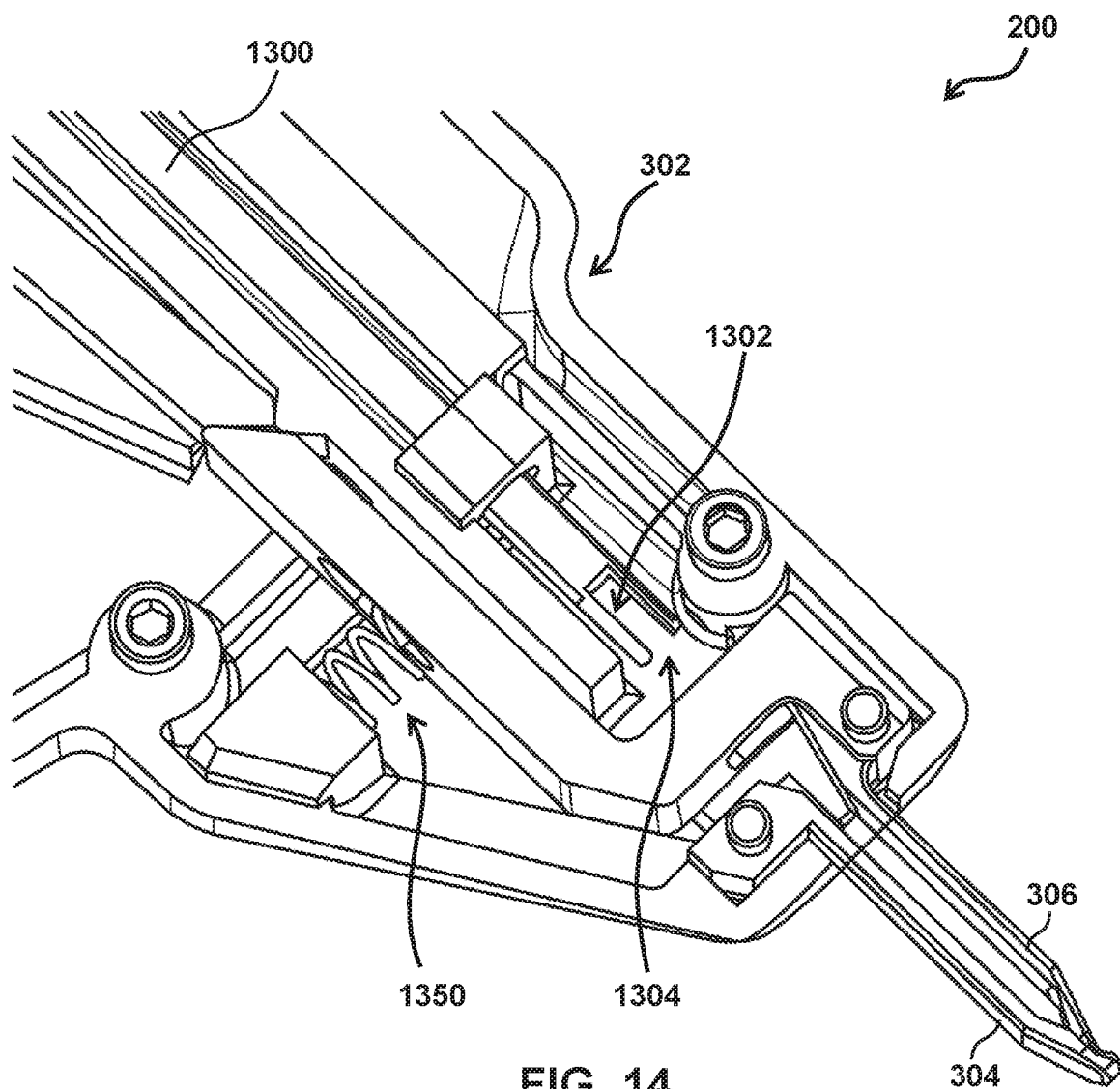
FIG. 14 illustrates another view of the exemplary implementation of the component advancer including the pusher tube coupled with the handle of the delivery system, in accordance with certain aspects of the disclosure.

FIGS. 13 and 14 illustrate different views of an exemplary implementation of a component advancer 302 including a pusher tube 1300 coupled with handle 300. As shown in FIG. 13, in some implementations, pusher tube 1300 may include a notch 1302 having a shape complementary to a portion of a component and configured to maintain the component in a particular orientation so as to avoid rotation of the component within system 200. FIG. 13 shows notch 1302 formed in a distal end 1304 of pusher tube 1300 configured to mate and/or otherwise engage with an end of a distal portion of a component (not shown in FIG. 13) to be implanted. Pusher tube 1300 may be configured to push, advance, and/or otherwise propel a component toward and/or into a patient via notch 1302 responsive to actuation of handle 300.

In some implementations, the proximal end 1308 of pusher tube 1300 may be coupled to handle 300 via a joint 1310. Joint 1310 may be configured to translate articulation of handle 300 by an operator into movement of pusher tube 1300 toward a patient. Joint 1310 may include one or more of a pin, an orifice, a hinge, and/or other components. In some implementations, component advancer 302 may include one or more guide components 1314 configured to guide pusher tube 1300 toward the patient responsive to the motion translation by joint 1310. In some implementations, guide components 1314 may include sleeves, clamps, clips, elbow shaped guide components, and/or other guide components. Guide components 1314 may also add a tensioning feature to ensure the proper tactile feedback to the physician during deployment. For example, if there is too much resistance through guide components 1314, then the handle 300 will be too difficult to move. Additionally, if there is too little resistance through the guide components 1314, then the handle 300 will have little tension and may depress freely to some degree when delivery system 200 is inverted.

FIG. 14 provides an enlarged view of distal end 1304 of pusher tube 1300. As shown in FIG. 14, notch 1302 is configured with a rectangular shape. This rectangular shape is configured to mate with and/or otherwise engage a corresponding rectangular portion of a component (e.g., as described below). The rectangular shape is configured to maintain the component in a specific orientation. For example, responsive to a component engaging pusher tube 1300 via notch 1302, opposing (e.g., parallel in this example) surfaces, and/or the perpendicular (in this example) end surface of the rectangular shape of notch 1302 may be configured to prevent rotation of the component. This notch shape is not intended to be limiting. Notch 1302 may have any shape that allows it to engage a corresponding portion of a component and prevent rotation of the component as described herein. For example, in some implementations, pusher tube 1300 may include one or more coupling features (e.g., in addition to or instead of the notch) configured to engage the portion of the component and configured to maintain the component in a particular orientation so as to avoid rotation of the component within system 200. These coupling features may include, for example, mechanical pins on either side of the pusher tube 1300 configured to mate with and/or otherwise engage receptacle features on a corresponding portion of a component.

Figure 15:
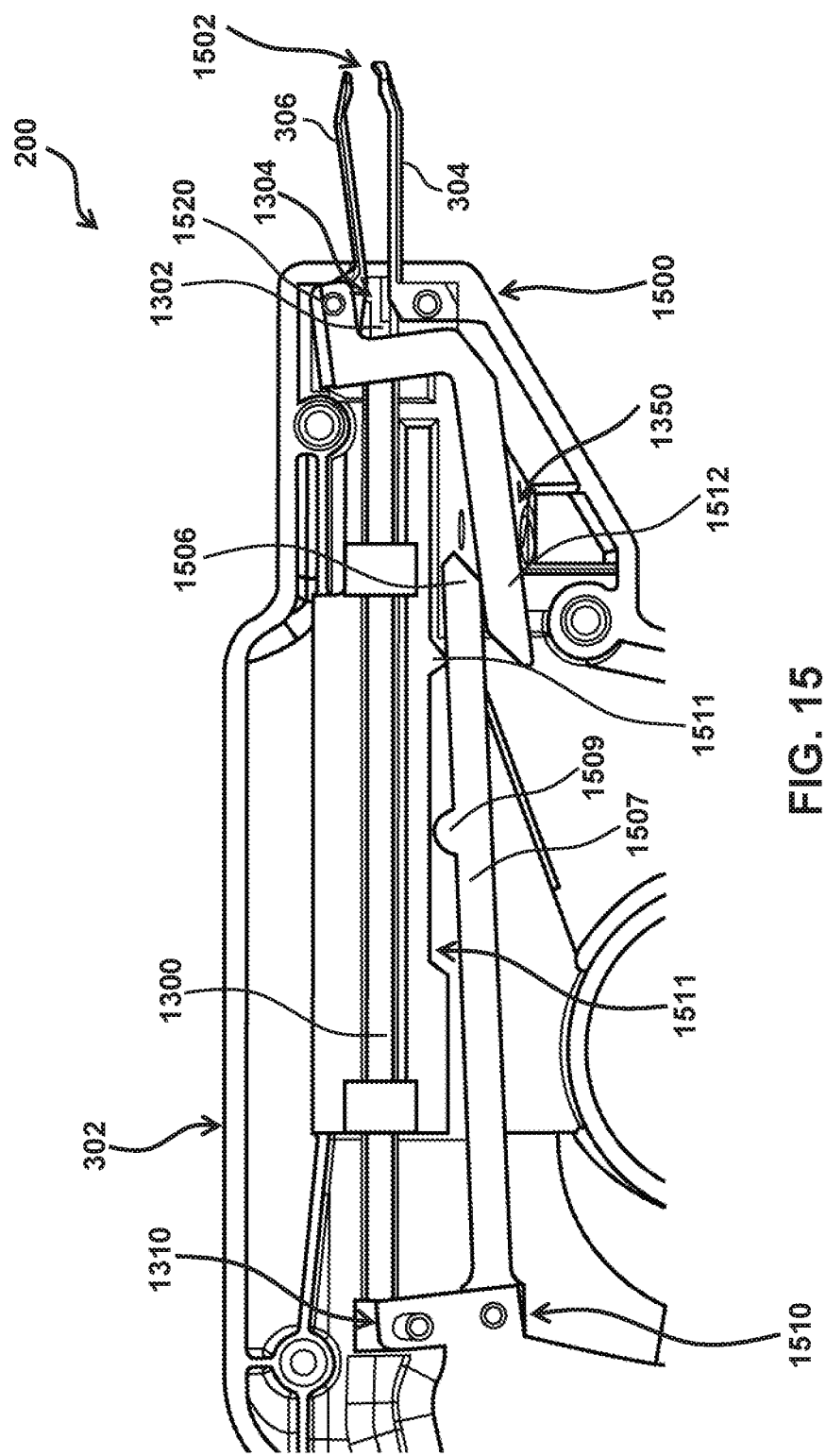
FIG. 15 illustrates the exemplary insertion tips in an open position, in accordance with certain aspects of the disclosure.

FIG. 15 illustrates insertion tips 304 and 306 in an open position 1502. FIG. 15 also illustrates pusher tube 1300 in an advanced position 1500, caused by actuation of handle 300 (not shown). Advanced position 1500 of pusher tube 1300 may be a position that is closer to insertion tips 304, 306 relative to the position of pusher tube 1300 shown in FIG. 14.

In some implementations, the component advancer 302 may include a wedge 1506 configured to move insertion tip 304 and/or 306 to the open position 1502. In some implementations, wedge 1506 may be configured to cause movement of the moveable insertion tip 306 and may or may not cause movement of insertion tip 304.

Wedge 1506 may be coupled to handle 300, for example, via a joint 1510 and/or other components. Joint 1510 may be configured to translate articulation of handle 300 by an operator into movement of the wedge 1506. Joint 1510 may include one or more of a pin, an orifice, a hinge, and/or other components. Wedge 1506 may be designed to include an elongated portion 1507 configured to extend from joint 1510 toward insertion tip 306. In some implementations, wedge 1506 may include a protrusion 1509 and/or other components configured to interact with corresponding parts 1511 of component advancer 302 to limit a travel distance of wedge 1506 toward insertion tip 306 and/or handle 300.

Wedge 1506 may also be slidably engaged with a portion 1512 of moveable insertion tip 306 such that actuation of handle 300 causes wedge 1506 to slide across portion 1512 of moveable insertion tip 306 in order to move moveable insertion tip 306 away from fixed insertion tip 304. For example, insertion tip 306 may be coupled to component advancer 302 via a hinge 1520. Wedge 1506 sliding across portion 1512 of moveable insertion tip 306 may cause moveable insertion tip to rotate about hinge 1520 to move moveable insertion tip 306 away from fixed insertion tip 304 and into open position 1502. In some implementations, moveable insertion tip 306 may be biased to a closed position. For example, a spring mechanism 1350 (also labeled in FIGS. 13 and 14) and/or other mechanisms may perform such biasing for insertion tip 306. Spring mechanism 1350 may force insertion tip 306 into the closed position until wedge 1506 is advanced across portion 1512, thereby separating insertion tip 306 from insertion tip 304.

In some implementations, as described above, first insertion tip 304 and second insertion tip 306 may be moveable. In some implementations, first insertion tip 304 and/or second insertion tip 306 may be biased to a closed position. For example, a spring mechanism similar to and/or the same as spring mechanism 1350 and/or other mechanisms may perform such biasing for first insertion tip 304 and/or second insertion tip 306. In such implementations, system 200 may comprise one or more wedges similar to and/or the same as wedge 1506 configured to cause movement of first and second insertion tips 304, 306. The one or more wedges may be coupled to handle 300 and slidably engaged with first and second insertion tips 304, 306 such that actuation of handle 300 may cause the one or more wedges to slide across one or more portions of first and second insertion tips 304, 306 to move first and second insertion tips 304, 306 away from each other.

In some implementations, system 200 may comprise a spring/lock mechanism or a rack and pinion system configured to engage and cause movement of moveable insertion tip 306. The spring/lock mechanism or the rack and pinion system may be configured to move moveable insertion tip 306 away from fixed insertion tip 304, for example. A spring lock design may include design elements that force the separation of insertion tips 304 and 306. One such example may include spring forces that remain locked in a compressed state until the component advancer or separating wedge activate a release trigger, thereby releasing the compressed spring force onto insertion tip 306, creating a separating force. These spring forces must be of sufficient magnitude to create the desired separation of tips 304 and 306 in the biological tissue. Alternatively, the spring compression may forceable close the insertion tips until the closing force is released by the actuator. Once released, the tips are then driven to a separating position by the advancement wedge mechanism, as described herein.

In some implementations, the component delivered by delivery system 200 (e.g., described above) may be an electrical lead for implantation in the patient. The lead may comprise a distal portion, one or more electrodes, a proximal portion, and/or other components. The distal portion may be configured to engage component advancer 302 of delivery system 200 (e.g., via notch 1302 shown in FIGS. 13 and 14). The distal portion may comprise the one or more electrodes. For example, the one or more electrodes may be coupled to the distal portion. The one or more electrodes may be configured to generate therapeutic energy for biological tissue of the patient. The therapeutic energy may be, for example, electrical pulses and/or other therapeutic energy. The biological tissue may be the heart (e.g., heart 118 shown in FIG. 1-FIG. 2C) and/or other biological tissue. The proximal portion may be coupled to the distal portion. The proximal portion may be configured to engage a controller when the lead is implanted in the patient. The controller may be configured to cause the one or more electrodes to generate the therapeutic energy, and/or perform other operations.

Figure 16:
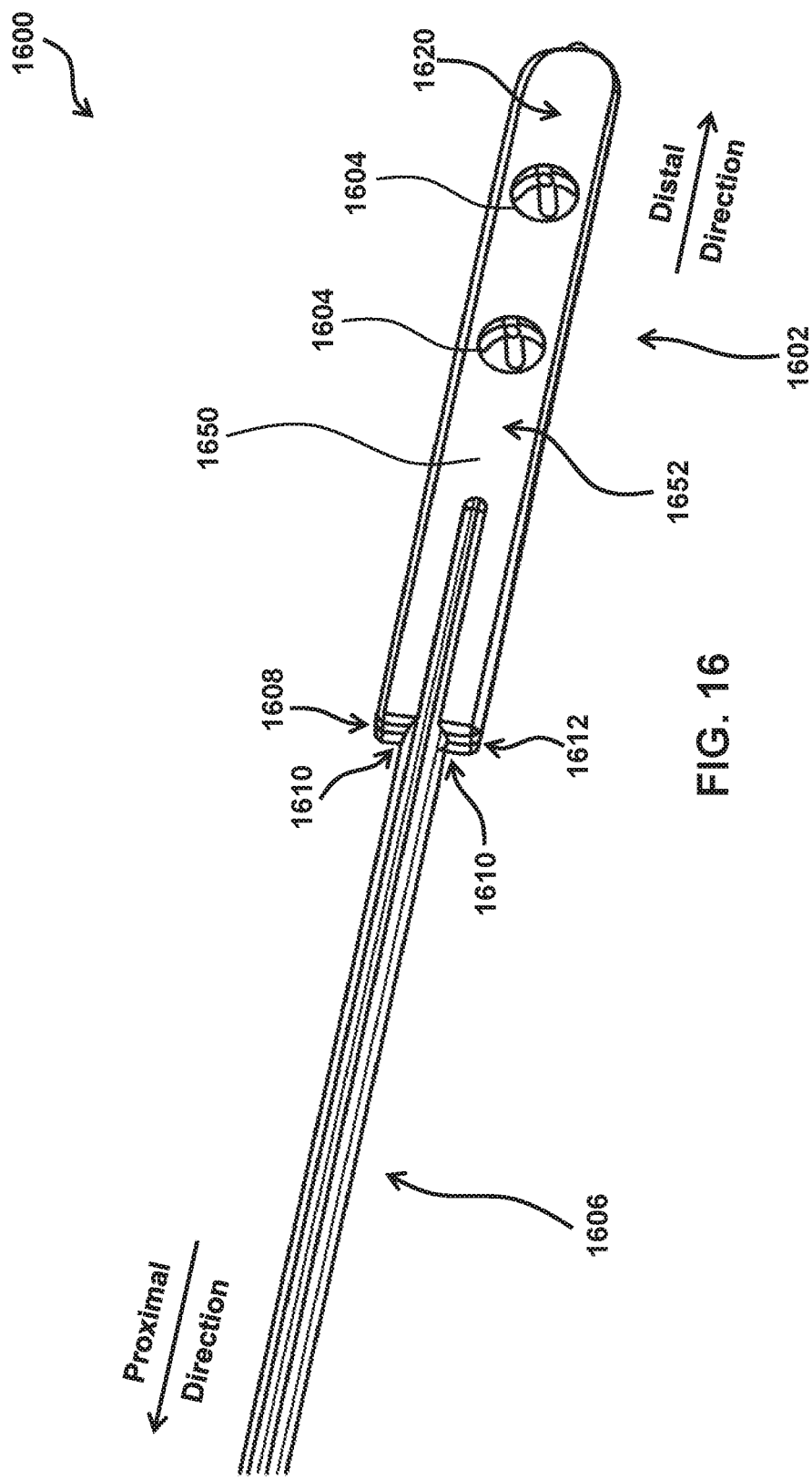
FIG. 16 illustrates an example implementation of an electrical lead, in accordance with certain aspects of the disclosure.

FIG. 16 illustrates an example implementation of an electrical lead 1600. Lead 1600 may comprise a distal portion 1602, one or more electrodes 1604, a proximal portion 1606, and/or other components. Distal portion 1602 may be configured to engage component advancer 302 of delivery system 200 (e.g., via notch 1302 shown in FIGS. 13 and 14). In some implementations, distal portion 1602 may comprise a proximal shoulder 1608. Proximal shoulder may be configured to engage component advancer 302 (e.g., via notch 1302 shown in FIGS. 13 and 14) such that lead 1600 is maintained in a particular orientation when lead 1600 is advanced into the patient. For example, in some implementations, proximal shoulder 1608 may comprise a flat surface 1610 (e.g., at a proximal end of distal portion 1602). In some implementations, proximal shoulder 1608 may comprise a rectangular shape 1612. Flat surface 1610 and/or rectangular shape 1612 may be configured to correspond to a (e.g., rectangular) shape of notch 1302 shown in FIGS. 13 and 14. In some implementations, transition surfaces between flat surface 1610 and other portions of distal portion 1602 may be chamfered, rounded, tapered, and/or have other shapes.

In some implementations, proximal shoulder 1608 may include one or more coupling features configured to engage component advancer 302 to maintain the lead in a particular orientation so as to avoid rotation of the lead when the lead is advanced into the patient. In some implementations, these coupling features may include receptacles for pins included in pusher tube 1300, clips, clamps, sockets, and/or other coupling features.

In some implementations, proximal shoulder 1608 may comprise the same material used for other portions of distal portion 1602. In some implementations, proximal shoulder may comprise a more rigid material, and the material may become less rigid across proximal shoulder 1608 toward distal end 1620 of distal portion 1602.

In some implementations, proximal shoulder 1608 may function as a fixation feature configured to make removal of lead 1600 from a patient (and/or notch 1302) more difficult. For example, when lead 1600 is deployed into the patient, lead 1600 may enter the patient led by a distal end 1620 of the distal portion 1602. However, retracting lead 1600 from the patient may require the retraction to overcome the flat and/or rectangular profile of flat surface 1610 and/or rectangular shape 1612, which should be met with more resistance. In some implementations, delivery system 200 (FIG. 3) may include a removal device comprising a sheath with a tapered proximal end that can be inserted over lead 1600 so that when it is desirable to intentionally remove lead 1600, the flat and/or rectangular profile of shoulder 1608 does not interact with the tissue on the way out.

Figure 17:
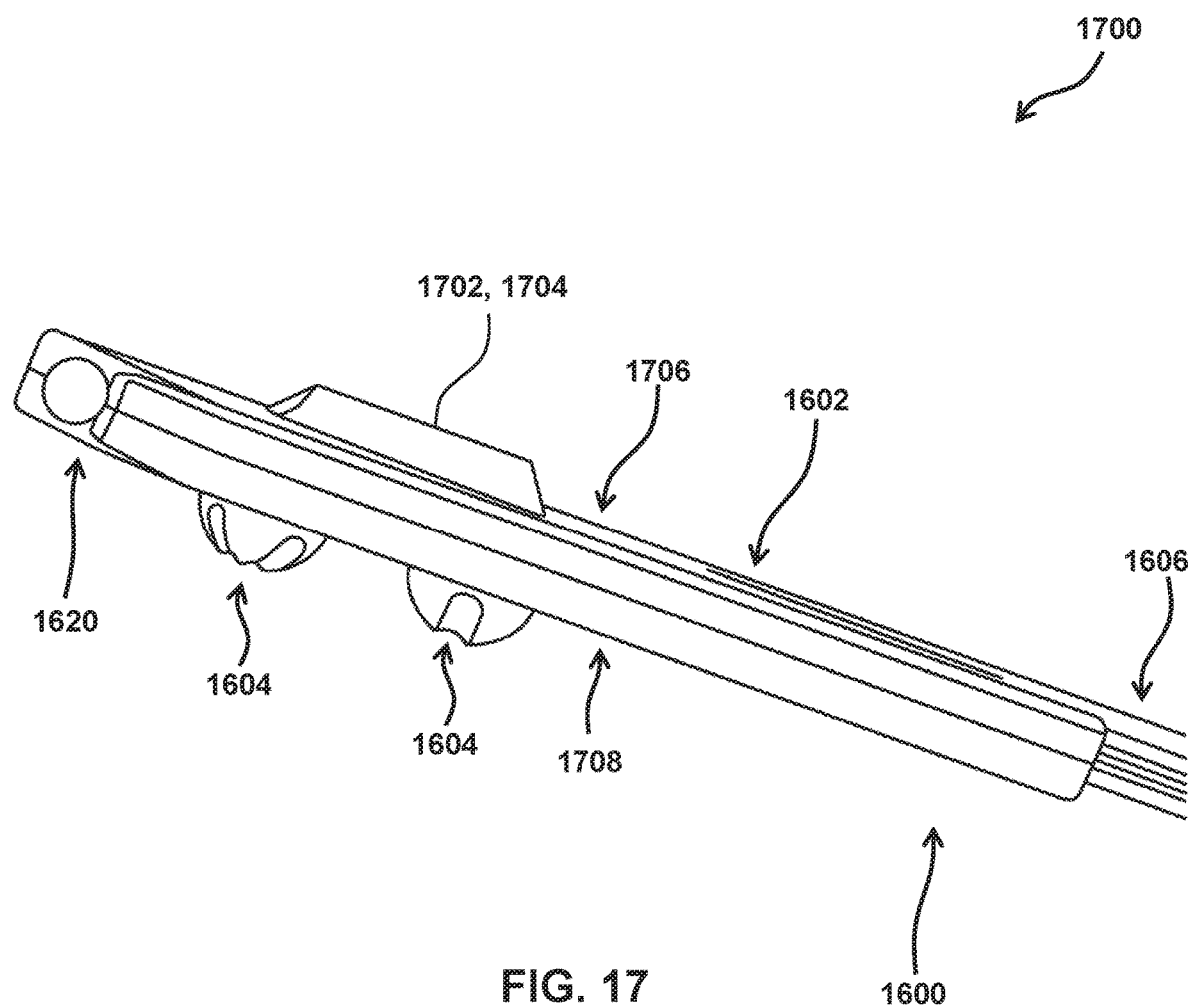
FIG. 17 illustrates another example implementation of an electrical lead, in accordance with certain aspects of the disclosure.

FIG. 17 illustrates another example implementation 1700 of electrical lead 1600. In some implementations, as shown in FIG. 17, distal portion 1602 may include one or more alignment features 1702 configured to engage delivery system 200 (FIG. 3) in a specific orientation. For example, alignment features 1702 of lead 1600 may include a rib 1704 and/or other alignment features configured to engage a groove in a channel (e.g., channel 500 shown in FIG. 5) of insertion tip 304 and/or 306 (FIG. 5). Rib 1704 may be on an opposite side 1706 of the lead 1600 relative to a side 1708 with electrodes 1604, for example. These features may enhance the guidance of lead 1600 through channel 500, facilitate alignment of lead 1600 in channel 500 (e.g., such that electrodes 1604 are oriented in a specific direction in tips 304, 306), prevent lead 1600 from exiting tips 304, 306 to one side or the other (as opposed to exiting out ends 404, 406 shown in FIG. 4), and/or have other functionality.

In some implementations, rib 1704 may be sized to be just large enough to fit within the groove in the channel 500. This may prevent the lead from moving within the closed insertion tips 304, 306 while the insertion tips are pushed through the intercostal muscle tissue. Additionally, rib 1704 may prevent an operator from pulling lead 1600 too far up into delivery system 200 (FIG. 3) when loading delivery system 200 with a lead (e.g., as described below). This may provide a clinical benefit, as described above, and/or have other advantages.

Figure 18:
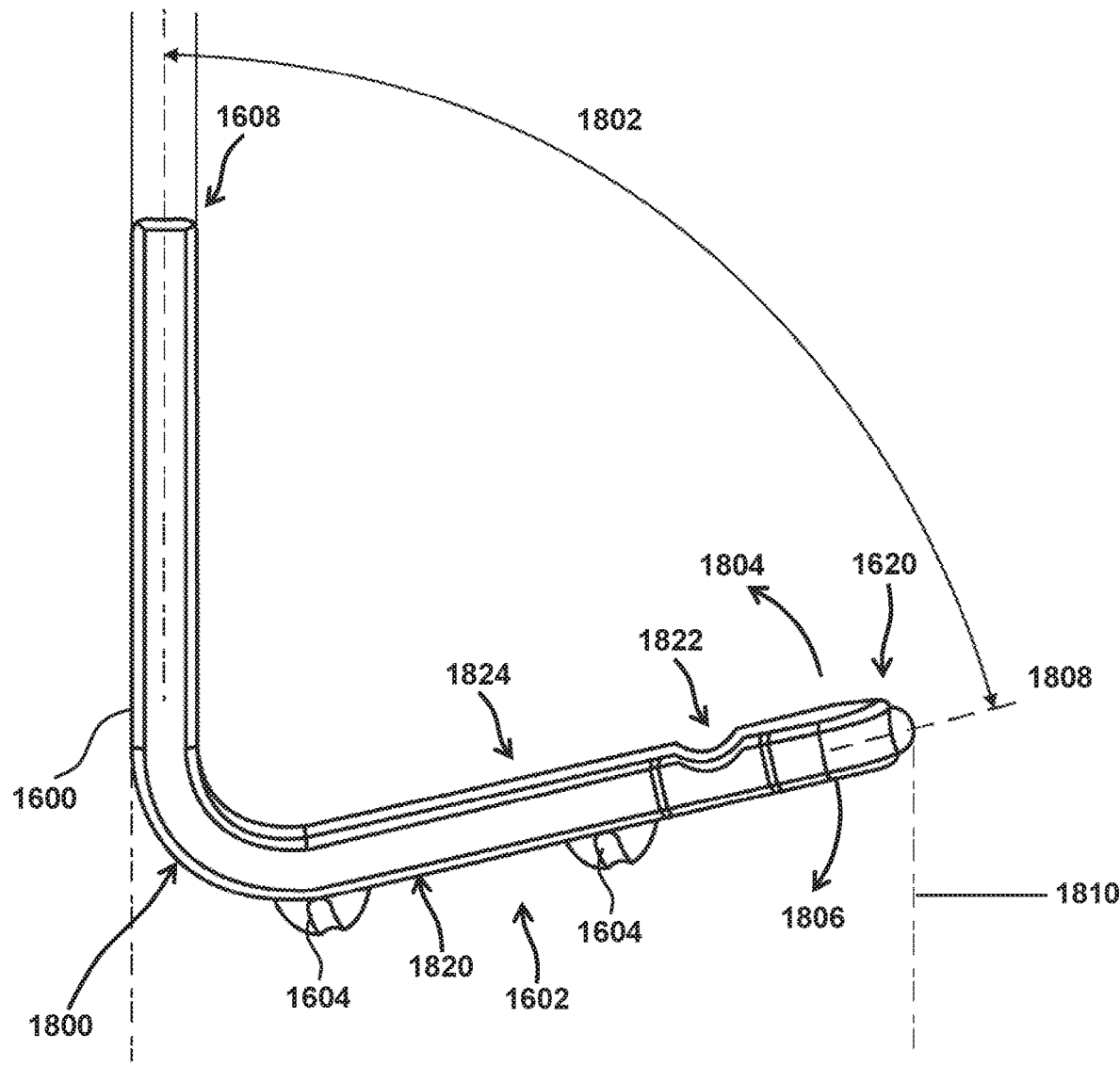
FIG. 18 illustrates a distal portion of an exemplary electrical lead bent in a predetermined direction, in accordance with certain aspects of the disclosure.

FIG. 18 illustrates distal portion 1602 of lead 1600 bent 1800 in a predetermined direction 1804. In some implementations, distal portion 1602 may be preformed to bend in predetermined direction 1804. The pre-forming may shape set distal portion 1602 with a specific shape, for example. In the example, shown in FIG. 18, the specific shape may form an acute angle 1802 between ends 1620, 1608 of distal portion 1602. The pre-forming may occur before lead 1600 is loaded into delivery system 200 (FIG. 3), for example. In some implementations, distal portion 1602 may comprise a shape memory material configured to bend in predetermined direction 1804 when lead 1600 exits delivery system 200. The shape memory material may comprise nitinol, a shape memory polymer, and/or other shape memory materials, for example. The preforming may include shape setting the shape memory material in the specific shape before lead 1600 is loaded into delivery system 200.

Distal portion 1602 may be configured to move in an opposite direction 1806, from a first position 1808 to a second position 1810 when lead 1600 enters the patient. In some implementations, first position 1808 may comprise an acute angle 1802 shape. In some implementations, the first position may comprise a ninety degree angle 1802 shape, or an obtuse angle 1802 shape. In some implementations, the second position may comprise a ninety degree angle 1802 shape, or an obtuse angle 1802 shape. Distal portion 1602 may be configured to move from first position 1808 to second position 1810 responsive to the shape memory material being heated to body temperature or by removal of an internal wire stylet, for example. In some implementations, this movement may cause an electrode side of distal portion 1602 to push electrodes 1604 into tissues toward a patient's heart, rather than retract away from such tissue and the heart. This may enhance electrical connectivity and/or accurately delivering therapeutic energy toward the patient's heart, for example.

Figure 19:
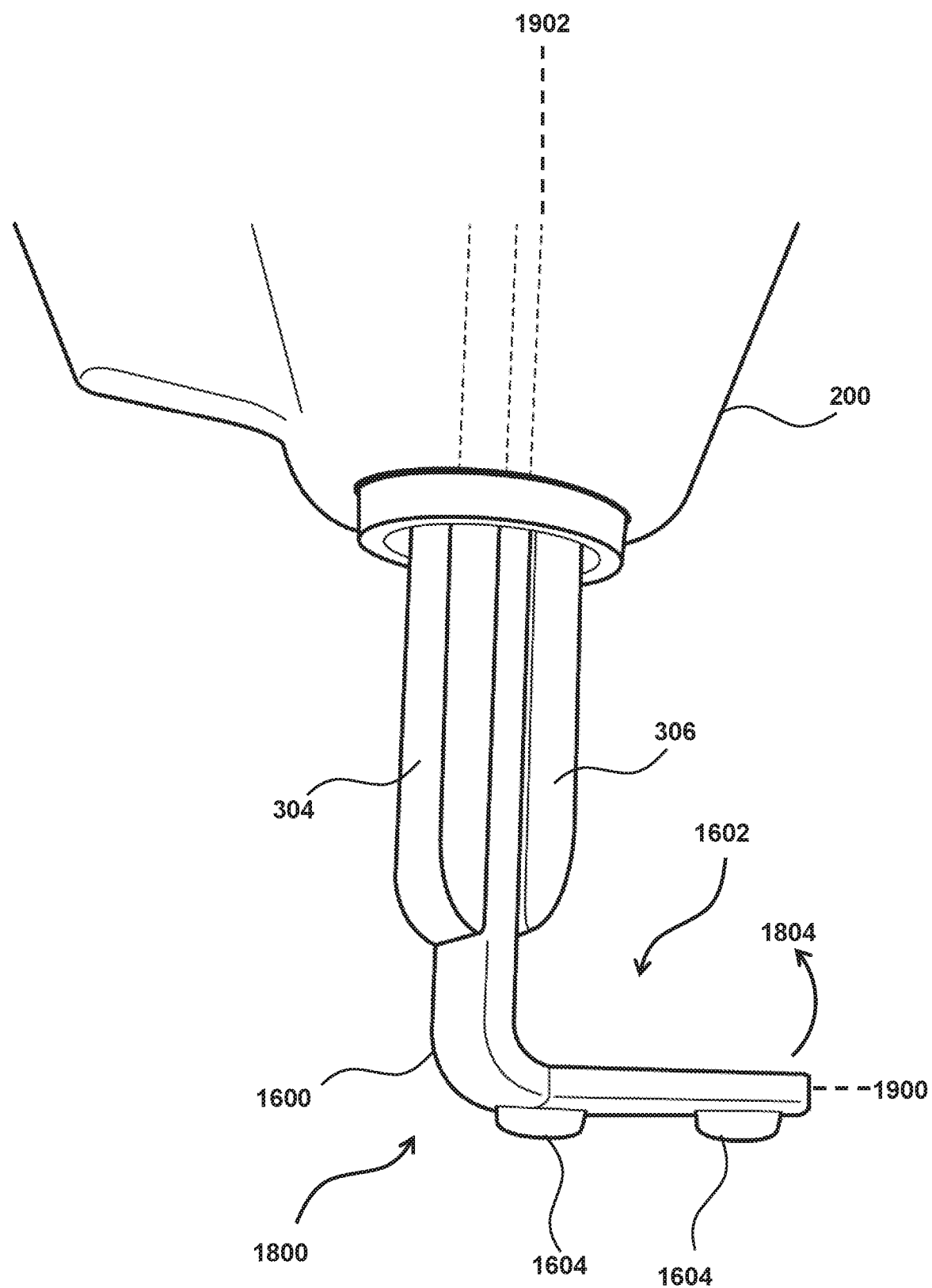
FIG. 19 illustrates the distal portion bending in the predetermined direction when the lead exits the delivery system, in accordance with certain aspects of the disclosure.

FIG. 19 illustrates distal portion 1602 bending 1800 in the predetermined direction 1804 when lead 1600 exits delivery system 200. In some implementations, as shown in FIG. 19, the predetermined direction may comprise a lateral and/or transverse direction 1900 relative to an orientation 1902 of insertion tips 304 and/or 306, a sternum of the patient, and/or other reference points in delivery system 200 and/or in the patient.

Figure 20:
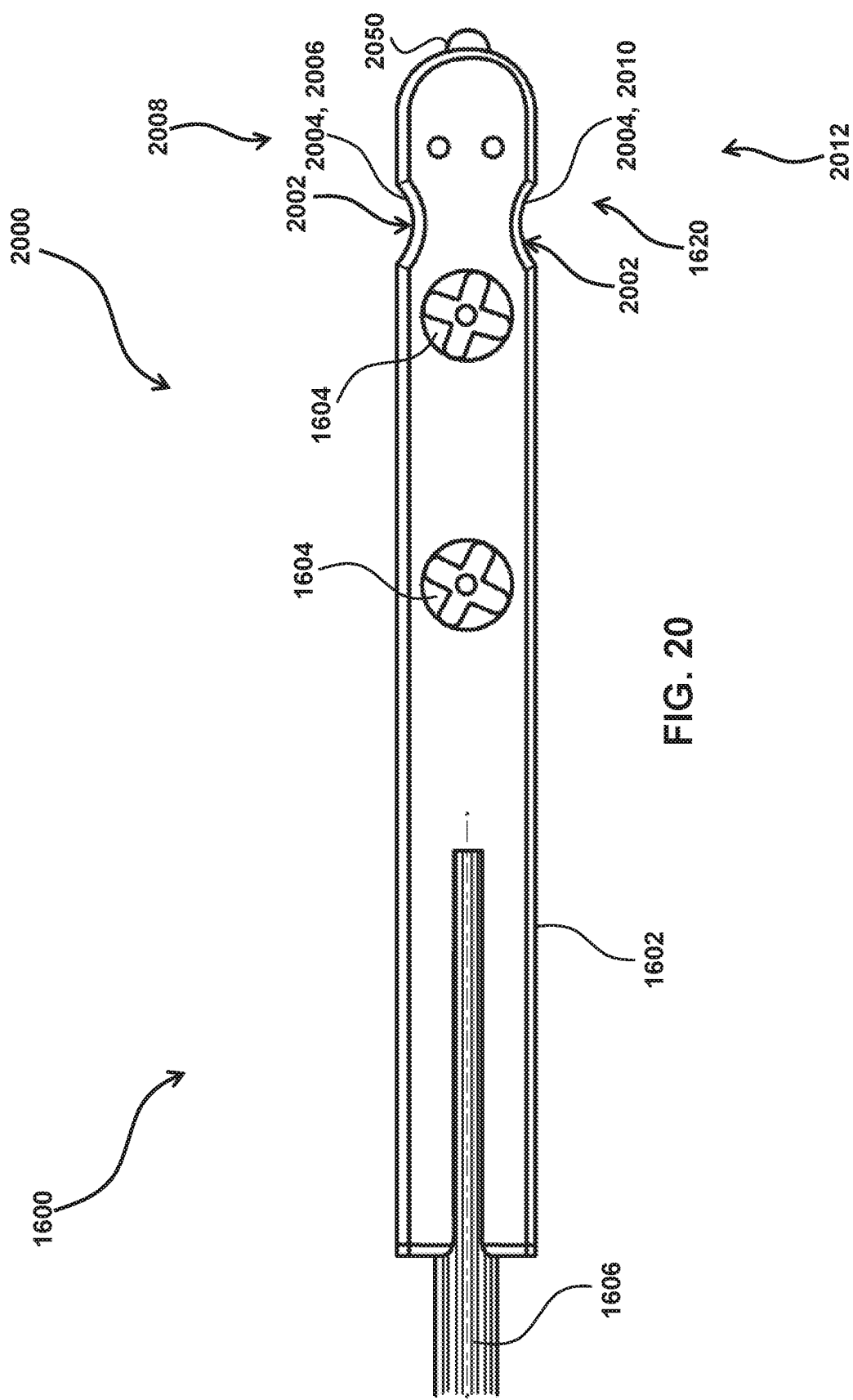
FIG. 20 illustrates an exemplary implementation of the distal portion of a lead, in accordance with certain aspects of the disclosure.
Figure 21:
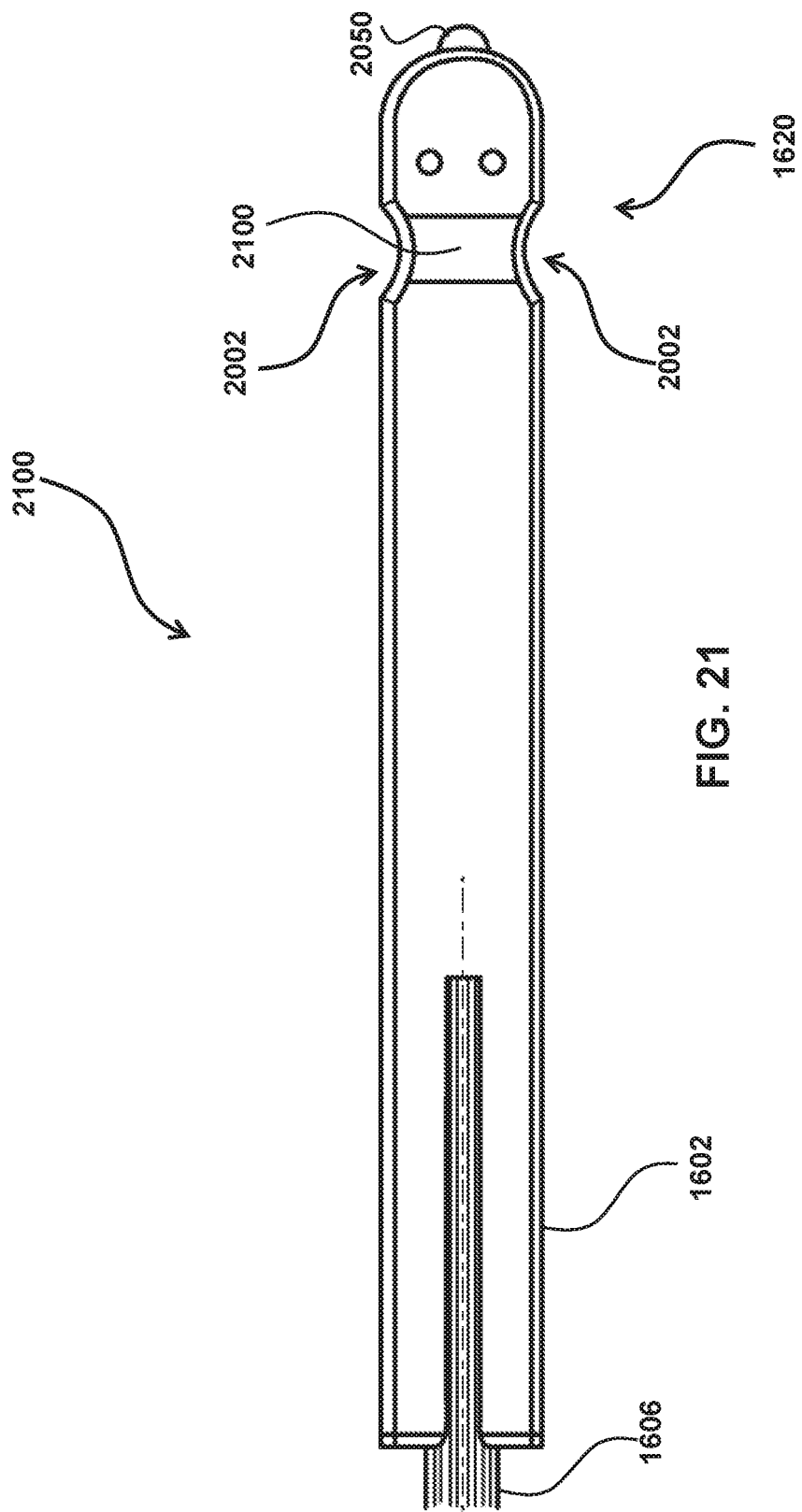
FIG. 21 illustrates another exemplary implementation of the distal portion of a lead, in accordance with certain aspects of the disclosure.

FIGS. 20 and 21 illustrate implementations 2000 and 2100 of distal portion 1602 of lead 1600. In some implementations, distal portion 1602 may include distal end 1620 and distal end 1620 may include a flexible portion 2002 so as to allow distal end 1620 to change course when encountering sufficient resistance traveling through the biological tissue of the patient. In some implementations, distal end 1620 may be at least partially paddle shaped, and/or have other shapes. The paddle shape may allow more surface area of distal end 1620 to contact tissue so the tissue is then exerting more force back on distal end 1620, making distal end 1620 bend and flex via flexible portion 2002. In some implementations, flexible portion 2002 may comprise a material that flexes more easily relative to a material of another area of distal portion 1602. For example, flexible portion 2002 may comprise a different polymer relative to other areas of distal portion 1602, a metal, and/or other materials.

In some implementations, flexible portion 2002 may comprise one or more cutouts 2004. The one or more cutouts 2004 may comprise one or more areas having a reduced cross section compared to other areas of distal portion 1602. The one or more cutouts 2004 may be formed by tapering portions of distal portion 1602, removing material from distal portion 1602, and/or forming cutouts 2004 in other ways. The cutouts may increase the flexibility of distal end 1620, increase a surface area of distal end 1620 to drive distal end 1620 in a desired direction, and/or have other purposes. Cutouts 2004 may reduce a cross-sectional area of distal end 1620, making distal end 1620 more flexible, and making distal end 1620 easier to deflect. Without such cutouts, for example, distal end 1620 may be too rigid or strong, and drive lead 1600 in a direction that causes undesirable damage to organs and/or tissues within the anterior mediastinum (e.g., the pericardium or heart).

In some implementations, the one or more areas having the reduced cross section (e.g., the cutouts) include a first area (e.g., cutout) 2006 on a first side 2008 of distal end 1620. The one or more areas having the reduced cross section (e.g., cutouts) may include first area 2006 on first side 2008 of distal end 1620 and a second area 2010 on a second, opposite side 2012 of distal end 1620. This may appear to form a neck and/or other features in distal portion 1602, for example.

In some implementations, as shown in FIG. 21, the one or more areas having the reduced cross section may include one or more cutouts 2100 that surround distal end 1620. Referring back to FIG. 18, in some implementations, distal portion 1602 may have a surface 1820 that includes one or more electrodes 1604, and a cut out 1822 in a surface 1824 of distal end 1620 opposite surface 1820 with one or more electrodes 1604. This positioning of cutout 1822 may promote a bias of distal end 1620 back toward proximal shoulder 1608 (FIG. 16) of lead 1600. In some implementations, cutout 1822 may create a bias (depending upon the location of cutout 2100) acutely in direction 1804 or obtusely in direction 1806. Similarly, alternative cutouts 2100 may be inserted to bias distal end 1620 in other directions.

Returning to FIGS. 20 and 21, in some implementations, flexible portion 2002 may be configured to cause distal end 1620 to be biased to change course in a particular direction. Distal end 1620 may change course in a particular direction responsive to encountering resistance from biological tissue in a patient, for example. In some implementations, biasing distal end 1620 to change course in a particular direction may comprise biasing distal end 1620 to maintain electrodes 1604 on a side of distal portion 1602 that faces the heart of the patient. For example, distal end 1620 may be configured to flex or bend to push through a resistive portion of biological material without twisting or rotating to change an orientation of electrodes 1604.

In some implementations, distal portion 1602 may include a distal tip 2050 located at a tip of distal end 1620. Distal tip 2050 may be smaller than distal end 1620. Distal tip 2050 may be more rigid compared to other portions of distal end 2050. For example, distal tip 2050 may be formed from metal (e.g., that is harder than other metal/polymers used for other portions of distal end 1620), hardened metal, a ceramic, a hard plastic, and/or other materials. In some implementations, distal tip 2050 may be blunt, but configured to push through biological tissue such as the endothoracic fascia, and/or other biological tissue. In some implementations, distal tip 2050 may have a hemispherical shape, and/or other blunt shapes that may still push through biological tissue.

In some implementations, distal tip 2050 may be configured to function as an electrode (e.g., as described herein). This may facilitate multiple sense/pace vectors being programmed and used without the need to reposition electrical lead 1600. For example, once the electrical lead 1600 is positioned, electrical connections can be made to the electrodes 1604 and cardiac pacing and sensing evaluations performed. If unsatisfactory pacing and/or sensing performance is noted, an electrical connection may be switched from one of the electrodes 1604 to the distal electrode 2050. Cardiac pacing and/or sensing parameter testing may then be retested between one of the electrodes 1604 and the distal electrode 2050. Any combination of two electrodes can be envisioned for the delivery of electrical therapy and sensing of cardiac activity, including the combination of multiple electrodes to create one virtual electrode, then used in conjunction with a remaining electrode or electrode pairing. Additionally, electrode pairing may be selectively switched for electrical therapy delivery vs. physiological sensing.

Returning to FIG. 16, in some implementations, at least a portion of distal portion 1602 of lead 1600 may comprise two parallel planar surfaces 1650. One or more electrodes 1604 may be located on one of the parallel planar surfaces, for example. Parallel planar surfaces 1650 may comprise elongated, substantially flat surfaces, for example. (Only one parallel planar surface 1650 is shown in FIG. 16. The other parallel planar surface 1650 may be located on a side of distal portion 1602 opposite electrodes 1604, for example.) In some implementations, at least a portion 1652 of distal portion 1602 of lead 1600 may comprise a rectangular prism including the two parallel planar surfaces 1650.

Because the proximal end of the distal portion 1602 may be positioned within the intercostal muscle tissue (while the distal end of the distal portion 1602 resides in the mediastinum), the elongated, substantially flat surfaces of proximal end of the distal portion 1602 may reduce and/or prevent rotation of distal portion 1602 within the muscle tissue and within the mediastinum. In contrast, a tubular element may be free to rotate. In some implementations, distal portion 1602 may include one or more elements configured to engage and/or catch tissue to prevent rotation, prevent egress and/or further ingress of distal portion 1602, and/or prevent other movement. Examples of these elements may include tines, hooks, and/or other elements that are likely to catch and/or hold onto biological tissue. In some implementations, the bending of distal portion 1602 (e.g., as described above related to FIG. 18) may also function to resist rotation and/or other unintended movement of distal portion 1602 in a patient. Distal portion 1602 may also be designed with multiple segments, with small separating gaps between each segment, designed to increase stability within the tissue, increase the force required for lead retraction or to promote tissue ingrowth within the distal portion 1602.

Figure 22:
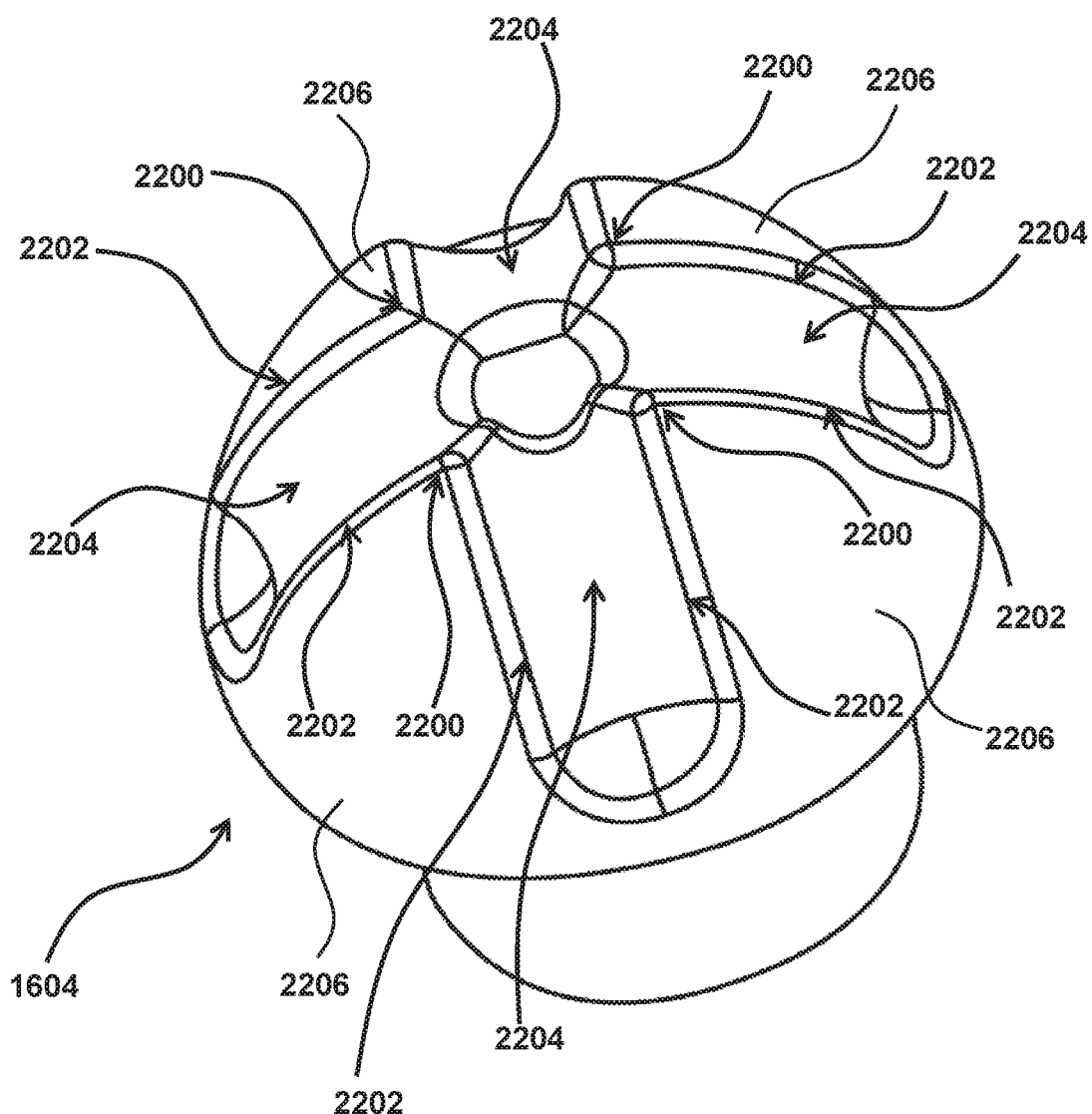
FIG. 22 illustrates an example of an electrode, in accordance with certain aspects of the disclosure.

FIG. 22 illustrates an example of an electrode 1604. In some implementations, an electrode 1604 may be formed from a conductive metal and/or other materials. Electrodes 1604 may be configured to couple with distal portion 1602 of lead 1600, proximal portion 1606 (e.g., wiring configured to conduct an electrical signal from a controller) of lead 1600, and/or other portions of lead 1600. In some implementations, distal portion 1602 may comprise a rigid material, with an area of distal portion 1602 around electrodes 1604 comprising a relatively softer material. One or more electrodes 1604 may protrude from distal portion 1602 of lead 1600 (e.g., as shown in FIG. 16). Electrodes 1604 may be configured to provide electrical stimulation to the patient or to sense electrical or other physiologic activity from the patient (e.g., as described above). In some implementations, one or more electrodes 1604 may include one or both of corners 2200 and edges 2202 configured to enhance a current density in one or more electrodes 1604. In some implementations, at least one of the electrodes 1604 may comprise one or more channels 2204 on a surface 2206 of the electrode 1604. In some implementations, at least one of the one or more electrodes 1604 may comprise two intersecting channels 2204 on surface 2206 of the electrode 1604. In some implementations, the channels 2204 may be configured to increase a surface area of an electrode 1604 that may come into contact with biological tissue of a patient. Other channel designs are contemplated.

Figure 23:
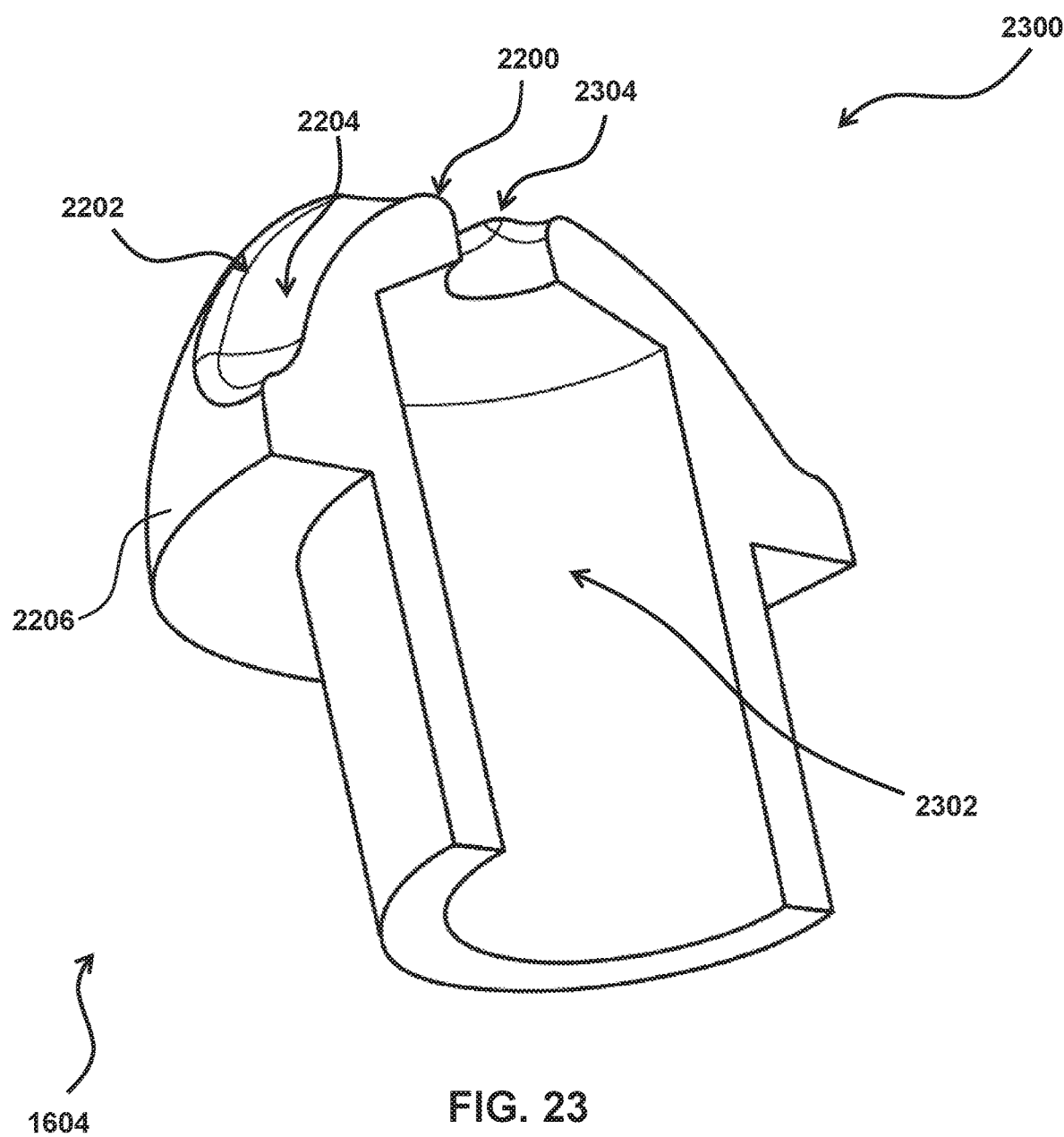
FIG. 23 illustrates a cross section of the example electrode, in accordance with certain aspects of the disclosure.

FIG. 23 illustrates a cross section 2300 of example electrode 1604. In some implementations, as shown in FIG. 23, at least one of the one or more electrodes 1604 may be at least partially hollow 2302. In such implementations, an electrode 1604 may include a hole 2304 configured to allow the ingress of fluid. In some implementations, an electrode 1604 may include a conductive mesh (not shown in FIG. 23) within hollow area 2302. The conductive mesh may be formed by conductive wiring, a porous sheet of conductive material, and/or other conductive meshes electrically coupled to electrode 1604. In some implementations, an electrode 1604 may include electrically coupled scaffolding within hollow area 2302. The scaffolding may be formed by one or more conductive beams and/or members placed in and/or across hollow area 2302, and/or other scaffolding.

These and/or other features of electrodes 1604 may be configured to increase a surface area and/or current density of an electrode 1604. For example, channels in electrodes 1604 may expose more surface area of an electrode 1604, and/or create edges and corners that increase current density, without increasing a size (e.g., the diameter) of an electrode 1604. The corners, hollow areas, conductive mesh, and/or scaffolding may function in a similar way.

In some implementations, an anti-inflammatory agent may be incorporated by coating or other means to electrode 1604. For example, a steroid material may be included in hollow area 2302 to reduce the patient's tissue inflammatory response.

As described above, in some implementations, system 200 (FIG. 3) includes the electrical lead 1600 (FIG. 16), handle 300 (FIG. 3), component advancer 302 (FIG. 3), first and second insertion tips 304, 306 (FIG. 3), and/or other components. First insertion tip 304 and second insertion tip 306 may be configured to close around a distal tip of the electrical lead when the electrical lead is placed within component advancer 302. First insertion tip 304 and second insertion tip 306 may be configured to push through biological tissue when in a closed position and to open to enable the electrical lead to exit from component advancer 302 into the patient. Component advancer 302, first insertion tip 304, and second insertion tip 306 may be configured to maintain the electrical lead in a particular orientation during the exit of the component from component advancer 302 into the patient. Also as described above, first insertion tip 304 may include a ramped portion configured to facilitate advancement of the component into the patient in a particular direction, and/or the electrical lead may be configured to bend in a predetermined direction after the exit of the component from the component advancer (e.g., because of its shape memory properties, etc.).

Figure 24:
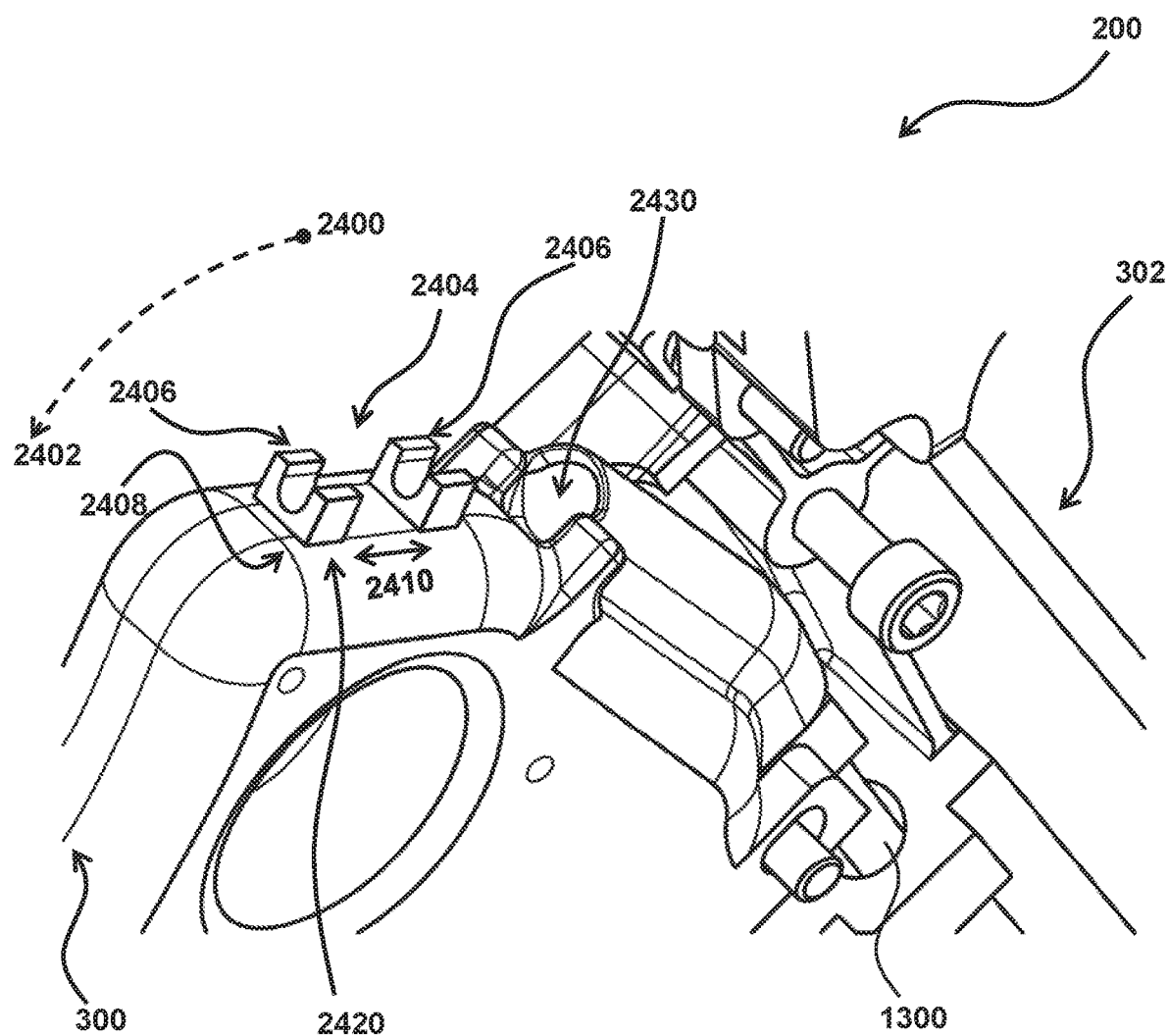
FIG. 24 illustrates exemplary components of a delivery system configured to load (or reload) a component (e.g., an electrical lead) into the delivery system, in accordance with certain aspects of the disclosure.

FIG. 24 illustrates components of delivery system 200 configured to load (or reload) a component (e.g., an electrical lead 1600 shown in FIG. 16) into delivery system 200. In some implementations, to facilitate reloading delivery system 200, an operator may thread proximal portion 1606 (FIG. 16) of lead 1600 backwards through insertion tips 304, 306 (FIG. 3), through pusher tube 1300 (in an implementation shown in FIG. 13) and out through an opening 2430 in handle 300. In some implementations, component advancer 302 may be configured to reload a component (e.g., an electrical lead) into delivery system 200. In such implementations, handle 300 may be configured to move from an advanced position 2400 to a retracted position 2402 to facilitate the reload of the component (e.g., the electrical lead).

In some implementations, handle 300 may include a dock 2404 configured to engage an alignment block coupled with the component (e.g., electrical lead) such that, responsive to handle 300 moving from advanced position 2400 to retracted position 2402, the engagement between dock 2404 and the alignment block draws the component into delivery system 200 to reload delivery system 200. As a non-limiting example using the implementation of component advancer 302 shown in FIG. 13-14, once the alignment block and electrical lead are properly seated within dock 2404, handle 300 may be re-cocked (e.g., moved from position 2400 to position 2402), which draws distal portion 1602 of electrical lead 1600 into delivery system 200 and closes insertion tips 304, 306 (FIG. 3).

In some implementations, dock 2404 may comprise one or more alignment and/or locking protrusions 2406 (the example in FIG. 24 illustrates two protrusions 2406) located on a portion 2408 of handle 300 toward component advancer 302. Locking protrusions 2406 may have a "U" shaped channel configured to receive a wire portion (e.g., part of proximal portion 1606) of an electrical lead 1600 (FIG. 16). Locking protrusions 2406 may have a spacing 2410 that corresponds to a size of an alignment block on the wire portion of electrical lead 1600 and allows the alignment block to fit between locking protrusions 2406 (with the wire portions resting in the "U" shaped channels of locking protrusions 2406).

FIG. 25 illustrates an example of an alignment block 2500 coupled to proximal portion 1606 of an electrical lead 1600. Alignment block 2500 may have a cylindrical shape, for example, with a length matching spacing 2410 configured to fit between locking protrusions 2406 shown in FIG. 24.

Returning to FIG. 24, in some implementations, handle 300 may include an alignment surface 2420 configured to receive the proximal portion 1606 (FIG. 25) of electrical lead 1600 (FIG. 16) such that, responsive to handle 300 moving from the advanced position to the retracted position, the component is drawn into delivery system 200 to reload delivery system 200. In some implementations, alignment surface 2420 may be the same as surface 2408, but without locking protrusions 2406. In some implementations, an operator may hold proximal portion 1606 against alignment surface 2420, within a retention block 2406, with finger pressure while handle 300 moves from advanced position 2400 to retracted position 2402, for example. In some implementations, the alignment block 2500 may not be utilized.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;"

"one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. An electrical lead for implantation in a patient, the lead comprising:
    a distal portion comprising one or more electrodes, the one or more electrodes configured to generate therapeutic energy for biological tissue of the patient; and
    a proximal portion coupled to the distal portion, the proximal portion configured to engage a controller when the lead is implanted in the patient, the controller configured to cause the electrode to generate the therapeutic energy,
    wherein the distal portion includes a distal end and the distal end includes a flexible portion comprising one or more cutouts formed in one or more surfaces that are adapted to increase the flexibility of the distal end so as to allow the distal end to change course when encountering sufficient resistance traveling through the biological tissue of the patient,
    wherein the distal end is at least partially paddle-shaped, having a planar surface that includes at least one of the one or more electrodes and another planar surface opposite the planar surface, the one or more cutouts including a first cutout formed in a first planar side of the distal end and a second cutout formed in a second planar side opposite the first planar side.

2. The lead of claim 1, wherein the flexible portion comprises a material that flexes more easily relative to a material of another area of the distal portion.

3. The lead of claim 1, the one or more cutouts comprising one or more areas having a reduced cross section compared to other areas of the distal portion.

4. The lead of claim 1, wherein the flexible portion is configured to cause the distal end to be biased to change course in a particular direction.

5. The lead of claim 1, wherein the flexible portion comprises a different polymer relative to other areas of the distal portion.

6. The lead of claim 4, wherein the bias is configured maintain the one or more electrodes facing the heart of the patient.

* * * * *